US009011878B2

(12) United States Patent
Hampson et al.

(10) Patent No.: US 9,011,878 B2
(45) Date of Patent: Apr. 21, 2015

(54) **VACCINE STRAINS OF *BRACHYSPIRA HYODYSENTERIAE***

(75) Inventors: David J. Hampson, Bedfordale (AU); Tom La, Parkwood (AU); Matthew I. Bellgard, Attadale (AU); Nyree D. Phillips, Kalamunda (AU)

(73) Assignee: Spirogene Pty Ltd, Murdoch (AU)

( * ) Notice: Subject to any disclaimer, the term of this patent is extended or adjusted under 35 U.S.C. 154(b) by 0 days.

(21) Appl. No.: 13/129,375

(22) PCT Filed: Nov. 13, 2009

(86) PCT No.: PCT/AU2009/001482
§ 371 (c)(1),
(2), (4) Date: Aug. 18, 2011

(87) PCT Pub. No.: WO2010/054437
PCT Pub. Date: May 20, 2010

(65) Prior Publication Data
US 2011/0293661 A1    Dec. 1, 2011

Related U.S. Application Data

(60) Provisional application No. 61/115,509, filed on Nov. 17, 2008.

(30) Foreign Application Priority Data

Nov. 14, 2008   (AU) ................. 2008905922

(51) Int. Cl.
| | | |
|---|---|---|
| *A61K 39/02* | (2006.01) | |
| *C07H 21/04* | (2006.01) | |
| *C12Q 1/68* | (2006.01) | |
| *G01N 33/569* | (2006.01) | |
| *A61K 39/00* | (2006.01) | |

(52) U.S. Cl.
CPC ....... *A61K 39/0225* (2013.01); *A61K 2039/522* (2013.01); *C12Q 1/689* (2013.01); *G01N 33/56911* (2013.01); *G01N 2333/20* (2013.01); *G01N 2500/10* (2013.01)

(58) Field of Classification Search
None
See application file for complete search history.

(56) References Cited

U.S. PATENT DOCUMENTS

| | | | |
|---|---|---|---|
| 5,882,655 A | 3/1999 | ter Huurne | |
| 6,682,745 B1 * | 1/2004 | Jacobs et al. | ............... 424/244.1 |

FOREIGN PATENT DOCUMENTS

WO    98/20899 A1    5/1998

OTHER PUBLICATIONS

Herbert et al eds, The Dictionary of Immunology, "Definition of Vaccine", one page, Academic Press, 1995.*
Ellis, R.W. Chapter 29 of "Vaccines", Plotkin, S.A. et al. (eds) published by W. B. Saunders company (Philadelphia) in 1988.*
By Bergey's Manual of Systematic Bacteriology. Springer, New York, 2010. 2nd edition vol. 4, p. 539.*
Mysore et al. Lab Anim Sci Feb. 1992: 42(1):7-12.*
La et al. Veterinary Microbiology, 153:150-156, 2011.*
Harel et al. Can J Vet Res 1994; 58:302-305.*
Hudson, M.J., et al., "Swine Dysentery: Protection of Pigs by Oral and Parenteral Immunisation With Attenuated *Treponema hyodysenteriae*," Research in Veterinary Science 21(3):366-367, Nov. 1976.
International Search Report mailed Jan. 28, 2010, issued in corresponding PCT/AU2009/001482, filed Nov. 13, 2009, 1 page.
Achacha, M., et al., "Development of an Experimental Model Allowing Discrimination Between Virulent and Avirulent Isolates of *Serpulina* (*Treponema*) *hyodysenteriae*," Canadian Journal of Veterinary Research 60(1):45-49, Jan. 1996.
Hampson, D., "Detection and Strain Typing of *Brachyspira hyodysenteriae* to Support Swine Dysentery Eradication and Control," Report Prepared for the Co-operative Research Centre for an Internationally Competitive Pork Industry, Willaston, Australia, Jul. 2008, 39 pages.
Li, Z., et al., "Serotyping of Canadian Isolates of *Treponema hyodysenteriae* and Description of Two New Serotypes," Journal of Clinical Microbiology 29(12):2794-2797, Dec. 1991.
Bellgard, M.I., et al., "Genome Sequence of the Pathogenic Intestinal Spirochete *Brachyspira hyodysenteriae* Reveals Adaptations to Its Lifestyle in the Porcine Large Intestine," Public Library of Science One 4(3): e4641.1-e4641.12, 2009.
Stanton, T.B., et al., "Isolation, Oxygen Sensitivity, and Virulence of NADH Oxidase Mutants of the Anaerobic Spirochete *Brachyspira* (*Serpulina*) *hyodysenteriae*, Etiologic Agent of Swine Dysentery," Applied and Environmental Microbiology 65(11):5028-5034, 1999.
Supplemental European Search Report, mailed May 24, 2013, issued in corresponding European Patent Application No. EP20090825655, filed Nov. 13, 2009, 18 pages.

* cited by examiner

*Primary Examiner* — Oluwatosin Ogunbiyi
(74) *Attorney, Agent, or Firm* — Christensen O'Connor Johnson Kindness PLLC

(57) ABSTRACT

The present invention relates generally to vaccine strains of *Brachyspira hyodysenteriae*. In particular, the present invention relates to isolated live vaccine strains of *B. hyodysenteriae* lacking one or more virulence factors. The present invention also relates to methods of identifying and preparing vaccine strains, as well as vaccine compositions against diarrhoeal diseases and methods and kits for diagnosing same.

8 Claims, 6 Drawing Sheets

FIGURE 1

| ORF | Primer set | Primer name | Sequence (5'-3') | Binding site (nucleotide position) | SEQ ID NO |
|---|---|---|---|---|---|
| ORF 1 | 1 | ORF1-F16 | ACTGGAGTTGCTGGATTTATAGGATC | 16-41 | 13 |
|  |  | ORF1-R575 | AAGTCAGGTCTCTGTCTCTTTCC | 553-575 | 14 |
|  | 2 | ORF1-F65 | CAAATAAAGATCATACTGTTATAGGAATAG | 65-94 | 15 |
|  |  | ORF1-R661 | ATGTATAGTCACGCATAGTGG | 641-661 | 16 |
|  | 3 | ORF1-F240 | TGTAATACATTTAGCAGGATATGG | 240-263 | 17 |
|  |  | ORF1-R623 | GGTATAGGATTATTTTCAAGTATCAG | 598-623 | 18 |
| ORF 2 | 1 | ORF2-F60 | GTTCATACCATTTAGAAAAAGAAGAG | 60-65 | 19 |
|  |  | ORF2-R760 | GTTCATACCATTTAGAAAAAGAAGAG | 742-760 | 20 |
|  | 2 | ORF2-F120 | AGAACAAAACAACATAAAGCATC | 120-142 | 21 |
|  |  | ORF2-R325 | CATCAGTAAAACAAATATAATCCC | 302-325 | 22 |
|  | 3 | ORF2-F664 | CCTGAGCATTATGGACTTTC | 664-683 | 23 |
|  |  | ORF2-R903 | TGTACTGTCTGATTTTTTATGGTC | 880-903 | 24 |
| ORF 6 | 1 | ORF6-F225 | AAATGTAGAAGATATTGTATTGCC | 225-248 | 25 |
|  |  | ORF6-R641 | ACCTCTCCTATATGTTTTTTATACTTAG | 614-641 | 26 |
|  | 2 | ORF6-F412 | ATTACTACAAAATGTACTCTAAAATGTAAG | 412-441 | 27 |
|  |  | ORF6-R957 | CCATACTATATGACAAAAATAAAATCTAG | 929-957 | 28 |
|  | 3 | ORF6-F611 | TATCTAAGTATAAAAAACATATAGGAGAGG | 611-640 | 29 |
|  |  | ORF6-R1108 | CAGCACAAAACTCACATAGTG | 1088-1108 | 30 |
| ORF 7 | 1 | ORF7-F98 | AAATACTTGTCAATAATCTTAGTGG | 98-122 | 31 |
|  |  | ORF7-R1916 | TTTCATCATAAGCAAAAATAATATC | 1891-1916 | 32 |
|  | 2 | ORF7-F310 | GTAAGTGGAAAAAGAATGAAACATAC | 310-335 | 33 |
|  |  | ORF7-F1341 | AGATTGTCTTGACGAATAAAAG | 1320-1341 | 34 |
|  | 3 | ORF7-F961 | AATAAATATGACATTAAAGGAATAAAAATC | 961-990 | 35 |
|  |  | ORF7-R1765 | CTATTGTTAGTAGCAAAATAATAAAAATAC | 1736-1765 | 36 |
| ORF 8 | 1 | ORF8-F14 | TAAATGAAGTATATAATAAAAATGAAAAAG | 14-43 | 37 |
|  |  | ORF8-R179 | AATAAACATGAAGAATGGTGTC | 158-179 | 38 |
|  | 2 | ORF8-F86 | ATAAACCAAATGATTTATTAACTATACC | 86-113 | 39 |
|  |  | ORF8-R163 | GGTGTCTTAATGCTAATTTATATTCTAG | 136-163 | 40 |
|  | 3 | ORF8-F145 | AAATTAGCATTAAGACACCATTC | 145-167 | 41 |
|  |  | ORF8-R250 | CAAGTTTATTTAGTTTTCTTTTCTGAC | 224-250 | 42 |
| ORF 9 | 1 | ORF9-F47 | ATTTAGAAGATGTAATACCTTTAGAGG | 47-73 | 43 |
|  |  | ORF9-R295 | TCATTTTCGCTATATTTTTATTTAC | 271-295 | 44 |
|  | 2 | ORF9-F247 | TTATACAAAATAGGAGAGCCTTTAG | 247-271 | 45 |
|  |  | ORF9-R609 | ATCGCAATAATCTGAAAATG | 590-609 | 46 |
|  | 3 | ORF9-F730 | GTATGTACTTATCTTTTTTATTCTATTGTC | 730-759 | 47 |
|  |  | ORF9-R923 | CATATTGGATTTTTATCTCTATGTC | 899-923 | 48 |
| ORF 10 | 1 | ORF10-F20 | ATTGGATAGAACATAGAGGGAG | 20-41 | 49 |
|  |  | ORF10-R320 | ACTGTATCATTTGCTATTTCATTAG | 296-320 | 50 |
|  | 2 | ORF10-F381 | TATAAAAACTATAAGAATATCTCTACAAGG | 381-410 | 51 |
|  |  | ORF10-R747 | AACATATAAGGTATAAAATGGTTGAG | 722-747 | 52 |
|  | 3 | ORF10-F721 | CCTCAACCATTTTATACCTTATATG | 721-745 | 53 |
|  |  | ORF10-R904 | TAACTATATTTTCTCGTTTTCCTTG | 880-904 | 54 |

FIGURE 2

| Plasmid ORF | Putative Function | E-value |
| --- | --- | --- |
| ORF 1 | Nucleoside-diphosphate-sugar epimerase | 3.00E-58 |
| ORF 2 | Glycosyl transferase | 4.00E-49 |
| ORF 3 | Rhamnan synthesis protein F (RpgF) | 8.00E-24 |
| ORF 4 | Rhamnan synthesis protein F (RpgF) | 4.00E-41 |
| ORF 5 | Rhamnan synthesis protein F (RpgF) | 4.00E-14 |
| ORF 6 | Radical SAM domain protein | 4.00E-14 |
| ORF 7 | Hydrolase | 2.00E-90 |
| ORF 8 | Unknown | na |
| ORF 9 | Fe-S oxidoreductase | 1.00E-78 |
| ORF 10 | Fe-S oxidoreductase | 8.00E-31 |
| ORF 11 | Fe-S oxidoreductase | 6.00E-74 |
| ORF 12 | Fe-S oxidoreductase | 9.00E-80 |
| ORF 13 | Fe-S oxidoreductase | 1.00E-104 |
| ORF 14 | Glycosyl transferase (RfaG) | 6.00E-37 |
| ORF 15 | NAD-dependent epimerase/dehydratase | 6.00E-39 |
| ORF 16 | dTDP-4-dehydrorhamnose 3,5-epimerase | 9.00E-50 |
| ORF 17 | Fe-S oxidoreductase | 1.00E-128 |
| ORF 18 | Glucose-1-phosphate cytidylyltransferase | 5.00E-90 |
| ORF 19 | Unknown | na |
| ORF 20 | ATPases involved in chromosome partitioning | 4.00E-25 |
| ORF 21 | Unknown | na |
| ORF 22 | Putative replicative DNA helicase | 4.00E-12 |
| ORF 23 | Primase | 5.00E-23 |
| ORF 24 | Site-specific recombinase | 8.00E-27 |
| ORF 25 | Glycosyl transferase | 2.00E-09 |
| ORF 26 | Rhamnan synthesis protein F (RpgF) | 2.00E-20 |
| ORF 27 | dTDP-glucose 4,6-dehydratase | 1.00E-128 |
| ORF 28 | Glucose-1-phosphate thymidylyltransferase | 1.00E-112 |
| ORF 29 | dTDP-4-dehydrorhamnose reductase (RfbD) | 5.00E-78 |
| ORF 30 | dTDP-4-dehydrorhamnose 3,5-epimerase (RfbC) | 6.00E-62 |
| ORF 31 | β-1,4-N-acetylgalactosaminyltransferase | 4.00E-05 |
| ORF 32 | Glycosyl transferase | 9.00E-55 |

FIGURE 3

| ORF | Primer set | Primer name | Sequence (5'-3') | Binding site 1-21 (nucleotide position) | SEQ ID NO |
|---|---|---|---|---|---|
| ORF 11 | 1 | ORF11-F47 | ATAGAACACCTTTACAAGAAATAATACCTC | 47-76 | 55 |
| | | ORF11-R408 | CAATCCAGCATCTACCAAC | 390-408 | 56 |
| | 2 | ORF11-F412 | AAGATCAACATTTCAATAGAAGGTATC | 412-438 | 57 |
| | | ORF11-R800 | CAGCAAGCACTTATAGTTCCATTAG | 776-800 | 58 |
| | 3 | ORF11-F960 | TCAAATAGATGATATAGATGATTACG | 960-985 | 59 |
| | | ORF11-R1185 | AATAGTAGAACTAAAATAAAAAAACCTATG | 1156-1185 | 60 |
| ORF 12 | 1 | ORF12-F31 | GAAACTAGGCATAAATTAGAAGAAG | 31-55 | 61 |
| | | ORF12-R977 | TCAGCATAATCATCTATATTATCTACTTG | 949-977 | 62 |
| | 2 | ORF12-F284 | TCAATATGGTTAAATATGCTAAAGATAGTG | 284-313 | 63 |
| | | ORF12-R395 | ATACCCGCATTTACTAATCCTTC | 373-395 | 64 |
| | 3 | ORF12-F377 | GATTAGTAAATGCGGGTATGAC | 377-398 | 65 |
| | | ORF12-R791 | AAAGCACATGGACTTACAGTAC | 770-791 | 66 |
| ORF 13 | 1 | ORF13-F50 | TAGAAACGGTAATCCCATTAG | 50-70 | 67 |
| | | ORF13-R372 | TAAAAGCGAAGCATTAGTAGTAG | 350-372 | 68 |
| | 2 | ORF13-F327 | TGATAAAGTAAATAGGGTAGATACTACTAC | 327-356 | 69 |
| | | ORF13-R747 | AAATACATAAGGACAAACCATTAC | 724-747 | 70 |
| | 3 | ORF13-F294 | TTTTGCTGAAATGGTAGAGTATG | 294-316 | 71 |
| | | ORF13-R852 | TATAGTTTTTACTGATTCTTTATTGACATC | 823-852 | 72 |
| ORF 14 | 1 | ORF14-F38 | TTGGTGGAGGAGTTGGTAC | 38-56 | 73 |
| | | ORF14-R275 | TGATAAAGAAGAGGATGATTCC | 254-275 | 74 |
| | 2 | ORF14-F331 | TCAGGTATAAATCCGCCTAATG | 331-352 | 75 |
| | | ORF14-R826 | CAGGTACTAAACCAGCAGTCATAG | 803-826 | 76 |
| | 3 | ORF14-F874 | GGTTTTATATGTAAGAATGAAGATG | 874-898 | 77 |
| | | ORF14-R1203 | CTTAGAATTTGAAGTCCAGTTTG | 1181-1203 | 78 |
| ORF 15 | 1 | ORF15-F79 | GAAGTTTTTGGCATAGGAAC | 79-98 | 79 |
| | | ORF15-R368 | TCATTTTCTTTTAATGGTGTATC | 346-368 | 80 |
| | 2 | ORF15-F216 | AAAAGGCTATTTAGAATCTGAAG | 216-238 | 81 |
| | | ORF15-R496 | CATTATCTCCATAAGTATAGAAAACTCTAC | 467-496 | 82 |
| | 3 | ORF15-F597 | TGGTGATATAGCAAAAGTATAGC | 597-620 | 83 |
| | | ORF15-R780 | CCCTACAATAATTTTAGGTTCTTCAG | 755-780 | 84 |
| ORF 16 | 1 | ORF16-F1 | GTGGGAAAAATAAATCTGAAG | Jan-21 | 85 |
| | | ORF16-R345 | GCTTAATTCTACAGTAAAATGCTG | 322-345 | 86 |
| | 2 | ORF16-F129 | GTAATGATGAACTTAAAAAATCAGGTATTG | 125-154 | 87 |
| | | ORF16-R395 | ATTCCATGAGCCACATAAGGAG | 374-395 | 88 |
| | 3 | ORF16-F166 | AAACAGTCAAATATGAGTTATAGTGC | 166-191 | 89 |
| | | ORF16-R557 | AAATCTGGTATACTTTTATCCTTTTC | 532-557 | 90 |

FIGURE 4

| ORF | Virulent strains possessing the plasmid | | | | | | | Avirulent strains possessing the plasmid | | | | | | Avirulent strains missing the plasmid | |
|---|---|---|---|---|---|---|---|---|---|---|---|---|---|---|---|
| | WA1 | B204 | Vic2 | BW1 | NSW5 | Q17 | NSW15 | B78$^T$ | SA2206 | VS1 | B234 | R301 | B6933 | FM 88.90 | A1 |
| ORF 1* | P | P | P | P | P | P | P | P | P | P | P | P | P | A | A |
| ORF 2* | P | P | P | P | P | P | P | P | P | P | P | P | P | A | A |
| ORF 3 | P | P | P | P | P | P | P | P | P | P | P | P | P | A | A |
| ORF 4 | P | P | P | P | P | P | P | P | P | P | P | P | P | A | A |
| ORF 5 | P | P | P | P | P | P | P | P | P | P | P | P | P | A | A |
| ORF 6* | P | P | P | P | P | P | P | P | P | P | P | P | P | A | A |
| ORF 7* | P | P | P | P | P | P | P | P | P | P | P | P | P | A | A |
| ORF 8* | P | P | P | P | P | P | P | P | P | P | P | P | P | A | A |
| ORF 9* | P | P | P | P | P | P | P | P | P | P | P | P | P | A | A |
| ORF 10* | P | P | P | P | P | P | P | P | P | P | P | P | P | A | A |
| ORF 11 | P | P | P | P | P | P | A | A | A | A | A | A | A | A | A |
| ORF 12 | P | P | P | P | P | P | A | A | A | A | A | A | A | A | A |
| ORF 13 | P | P | P | P | P | P | P | A | A | A | A | A | A | A | A |
| ORF 14 | P | P | P | P | P | P | P | A | A | A | A | A | A | A | A |
| ORF 15 | P | P | P | P | P | P | P | A | A | A | A | A | A | A | A |
| ORF 16 | P | P | P | P | P | P | P | A | A | A | A | A | A | A | A |
| ORF 17 | P | P | P | P | P | P | P | P | P | P | P | P | P | A | A |
| ORF 18 | P | P | P | P | P | P | P | P | P | P | P | P | P | A | A |
| ORF 19 | P | P | P | P | P | P | P | P | P | P | P | P | P | A | A |
| ORF 20 | P | P | P | P | P | P | P | P | P | P | P | P | P | A | A |
| ORF 21 | P | P | P | P | P | P | P | P | P | P | P | P | P | A | A |
| ORF 22 | P | P | P | P | P | P | P | P | P | P | P | P | P | A | A |
| ORF 23 | P | P | P | P | P | P | P | P | P | P | P | P | P | A | A |
| ORF 24 | P | P | P | P | P | P | P | P | P | P | P | P | P | A | A |
| ORF 25 | P | P | P | A | A | A | P | P | P | P | P | A | P | A | A |
| ORF 26 | P | P | P | P | P | P | P | P | P | P | P | P | P | A | A |
| ORF 27 | P | P | P | P | P | P | P | P | P | P | P | P | P | A | A |
| ORF 28 | P | P | P | P | P | P | P | P | P | P | P | P | P | A | A |
| ORF 29 | P | P | P | P | P | P | P | P | P | P | P | P | P | A | A |
| ORF 30 | P | P | P | P | P | P | P | P | P | P | P | P | P | A | A |
| ORF 31 | P | P | P | P | P | P | P | P | P | P | P | P | P | A | A |
| ORF 32 | P | P | P | P | P | P | P | P | P | P | P | P | P | A | A |

VACCINE STRAINS OF *BRACHYSPIRA HYODYSENTERIAE*

CROSS REFERENCE TO RELATED APPLICATION

This application claims the benefit of application Ser. No. 61/115,509, filed Nov. 17, 2008, the disclosure of which is incorporated herein by reference in its entirety.

STATEMENT REGARDING SEQUENCE LISTING

The sequence listing associated with this application is provided in test format in lieu of a paper copy and is hereby incorporated by reference into the specification. The name of the test file containing the sequence listing is 37115_SEQ_Final_US_2011-15-13.txt. The text file is 38 KB; was created on May 13, 2011; and is being submitted via EFS-Web with the filing of the application.

FIELD

The present invention relates generally to vaccine strains of *Brachyspira hyodysenteriae*.

INTRODUCTION

*Brachyspira hyodysenteriae* is an anaerobic intestinal spirochaete that infects a number of mammalian and avian species of animal and causes diarrhoeal diseases. A well studied example is swine dysentery (SD), a significant endemic disease of pigs in Australia and worldwide caused by *B. hyodysenteriae* infection in pigs. SD is a contagious mucohaemorrhagic diarrhoeal disease, characterised by extensive inflammation and necrosis of the epithelial, surface of the large intestine. Economic losses due to SD result mainly from growth retardation, costs of medication and mortality. Where SD is established in a piggery, the disease spectrum can vary from being mild, transient or unapparent, to being severe and even fatal.

Medication strategies in individual piggeries may mask clinical signs and in some piggeries SD may go unnoticed, or may only be suspected. Whether or not obvious SD occurs, *B. hyodysenteriae* may persist in infected pigs, or in other reservoir hosts such as rodents, or in the environment. All these sources pose potential for transmission of *B. hyodysenteriae* to uninfected herds.

A number of methods are employed to control SD, varying from the prophylactic use of antimicrobial agents, to complete destocking of infected herds and prevention of re-entry of infected carrier pigs. All these options are expensive and time consuming because to be fully effective they require the use of sophisticated diagnostic tests to monitor progress.

The "gold standard" for the control of diseases caused by *B. hyodysenteriae* would be the use of a vaccine to provide animals with immunity, preventing *B. hyodysenteriae* colonisation and/or disease. Historically, the most effective and efficacious vaccines have been live attenuated versions of virulent strains of microorganisms. These vaccines activate all phases of the immune response and provide durable immunity, i.e. boosters are not required.

Attempts have been made to develop vaccines against *B. hyodysenteriae* using immunogenic proteins and attenuated strains. However, killed whole cells of *B. hyodysenteriae* or subunits, administered intramuscularly to animals in experimental trials, were of little protective value. Additionally, while cloned recombinant periplasmic flagellar antigens appeared to confer protection in a mouse model of SD, the composition failed to provide protection in pigs. Currently there are no effective vaccines available for protection against *B. hyodysenteriae*.

SUMMARY

The inventors of the present invention have identified a number of *B. hyodysenteriae* virulence factors. These factors may be utilised in the development of vaccines comprising live *B. hyodysenteriae* strains.

Accordingly, in a first aspect the present invention provides an isolated live vaccine strain of *B. hyodysenteriae*, wherein said vaccine strain of *B. hyodysenteriae* lacks one or more virulence factors.

In some embodiments, the virulence factors are encoded by one or more polynucleotide sequences substantially similar to one or more of the nucleic acid sequences depicted in SEQ ID NO:1, SEQ ID NO:2, SEQ ID NO:3, SEQ ID NO:4, SEQ ID NO:5, or SEQ ID NO:6.

Accordingly, in a second aspect the present invention provides an isolated live vaccine strain of *B. hyodysenteriae*, wherein said vaccine strain of *B. hyodysenteriae* lacks one or more functional virulence factors encoded by one or more polynucleotide sequences substantially similar to one or more of the nucleic acid sequences depicted in SEQ ID NO:1, SEQ ID NO:2, SEQ ID NO:3, SEQ ID NO:4, SEQ ID NO:5, or SEQ ID NO:6.

In some embodiments, the isolated live vaccine strain of *B. hyodysenteriae* is an attenuated virulent strain, which comprises a modification that attenuates a virulence factor such that the strain retains its immunogenic properties so as to be protectively immunogenic, but is no longer virulent.

It will be appreciated by those skilled in the art that the attenuated virulent strain of *B. hyodysenteriae* may be modified in any way that results in the strain becoming attenuated or avirulent. For example, the modification may disrupt the function of the nucleic acids associated with virulence. In some embodiments, the modification results in the reduction or suppression of mRNA expression from one or more polynucleotide sequences substantially similar to one or more of the nucleic acid sequences depicted in SEQ ID NO:1, SEQ ID NO:2, SEQ ID NO:3, SEQ ID NO:4, SEQ ID NO:5, or SEQ ID NO:6, or combinations thereof. In some embodiments, the modification does not affect expression, but results in the translation of one or more non-functional products, wherein the functional products are encoded by one or more polypeptide sequences substantially similar to one or more of the amino acid sequences depicted in SEQ ID NO:7, SEQ ID NO:8, SEQ ID NO:9, SEQ ID NO:10, SEQ ID NO:11 or SEQ ID NO:12.

In some embodiments, the virulence factors are encoded by nucleic acid sequences that are plasmid-borne. As such, the modification may comprise curing the *B. hyodysenteriae* strain of one or more plasmids which comprise one or more of the virulence factors.

In other embodiments, the isolated live vaccine strain of *B. hyodysenteriae* is a naturally-occurring avirulent strain, which strain lacks one or more of the virulence factors encoded by a polynucleotide sequence substantially similar to one or more of the nucleic acid sequences depicted in SEQ ID NO:1, SEQ ID NO:2, SEQ ID NO:3, SEQ ID NO:4, SEQ ID NO:5, or SEQ ID NO:6.

In a third aspect the present invention provides a vaccine strain of *B. hyodysenteriae*, wherein said vaccine strain is a live strain of *B. hyodysenteriae* deficient in mRNA expression from one or more polynucleotide sequences substantially similar to one or more of the nucleic acid sequences depicted in SEQ ID NO:1, SEQ ID NO:2, SEQ ID NO:3, SEQ ID NO:4, SEQ ID NO:5, or SEQ ID NO:6 or combinations thereof, or expresses one or more non-functional products, wherein the functional products are encoded by one or more polypeptide sequences substantially similar to one or more of the amino acid sequences depicted in SEQ ID NO:7, SEQ ID NO:8, SEQ ID NO:9, SEQ ID NO:10, SEQ ID NO:11 or SEQ ID NO:12, wherein said strain has immunogenic properties so as to be protectively immunogenic.

In a fourth aspect the present invention provides a method of preparing a live vaccine strain of *B. hyodysenteriae* comprising: (a) selecting a virulent strain of *B. hyodysenteriae*; (b) producing a modification in said virulent strain of *B. hyodysenteriae* to provide a live attenuated virulent *B. hyodysenteriae* strain; (c) isolating the live attenuated virulent *B. hyodysenteriae* strain which contains said modification; and (d) selecting said isolated *B. hyodysenteriae* strain, wherein said selected *B. hyodysenteriae* strain retains its immunogenic properties so as to be protectively immunogenic.

In a fifth aspect the present invention provides a vaccine composition comprising in a pharmaceutically acceptable vehicle at least one vaccine strain of *B. hyodysenteriae* according to the first, second and/or third aspects of the invention.

In some embodiments, the vaccine composition additionally comprises an adjuvant.

In a sixth aspect the present invention provides a method of preventing a diarrhoeal disease in an animal comprising administering to said animal an effective amount of at least one vaccine strain according to the first, second and/or third aspects of the invention.

In a seventh aspect the present invention provides a method of diagnosing virulent *B. hyodysenteriae* colonization in an animal, comprising the steps of: (a) obtaining a sample from said animal; and (b) determining the presence or absence of one or more polynucleotide sequences substantially similar to one or more of the nucleic acid sequences depicted in SEQ ID NO:1, SEQ ID NO:2, SEQ ID NO:3, SEQ ID NO:4, SEQ ID NO:5, or SEQ ID NO:6 and/or the expression of corresponding mRNA or encoded protein products, wherein the presence of said nucleic acids or corresponding mRNA or protein products indicates the presence of virulent *B. hyodysenteriae* colonization in the animal.

In an eighth aspect the present invention provides a method of screening for compounds capable of inhibiting the virulence of *B. hyodysenteriae* comprising: (a) transfecting a cell with a DNA construct that comprises one or more polynucleotide sequences substantially similar to one or more of the nucleic acid sequences depicted in SEQ ID NO:1, SEQ ID NO:2, SEQ ID NO:3, SEQ ID NO:4, SEQ ID NO:5, or SEQ ID NO:6; (b) contacting said transfected cell with the candidate compound; (c) comparing the level of mRNA expression from one or more of said nucleic acid molecules or the level of protein encoded by said mRNA expression, wherein said protein has a polypeptide sequence substantially similar to one or more of the amino acid sequences depicted in SEQ ID NO:7, SEQ ID NO:8, SEQ ID NO:9, SEQ ID NO:10, SEQ ID NO:11 or SEQ ID NO:12, in the cell in the presence and absence of the candidate compound; and (d) inferring that the candidate compound is an inhibitor of *B. hyodysenteriae* virulence if there is significantly less mRNA and/or protein expression when the candidate compound is present compared to when the compound is absent.

It will be understood that the screening method of the present invention may alternatively comprise a DNA construct that encodes a reporter gene operatively linked to a transcriptional regulatory sequence or promoter of one or more polynucleotide sequences substantially similar to one or more of the nucleic acid sequences depicted in SEQ ID NO:1, SEQ ID NO:2, SEQ ID NO:3, SEQ ID NO:4, SEQ ID NO:5, or SEQ ID NO:6, wherein the candidate compound is an inhibitor of *B. hyodysenteriae* virulence if there is significantly less reporter gene product produced when the candidate compound is present compared to when the compound is absent.

In a ninth aspect the present invention provides the use of a vaccine strain of *B. hyodysenteriae* in the manufacture of a medicament used to prevent *B. hyodysenteriae* infection, comprising at least one vaccine strain according to the first, second and/or third aspects of the invention.

In a tenth aspect the present invention provides a kit for vaccination of an animal against *B. hyodysenteriae* infection comprising: (a) a vaccine composition comprising in a pharmaceutically acceptable vehicle at least one vaccine strain according to the first, second and/or third aspects of the invention; and (b) instructions for vaccinating an animal.

In an eleventh aspect the present invention provides a method of identifying a candidate vaccine strain of *B. hyodysenteriae* comprising the steps: (a) obtaining a sample of *B. hyodysenteriae*; and (b) determining the presence or absence of one or more of the nucleic acid molecules encoded by a polypeptide sequence as depicted in SEQ ID NO:1, SEQ ID NO:2, SEQ ID NO:3, SEQ ID NO:4, SEQ ID NO:5, SEQ ID NO:6 and/or the expression of corresponding mRNA or protein products, wherein the absence of said nucleic acids or expression of corresponding mRNA or protein is indicative of a vaccine strain of *B. hyodysenteriae*.

In a twelfth aspect the present invention provides a kit for diagnosing virulent *B. hyodysenteriae* colonization in an animal, comprising one or more PCR primers having polynucleotide sequences substantially similar to one or more of the nucleic acid sequences depicted in SEQ ID NOs:55-90.

BRIEF DESCRIPTION OF THE FIGURES

FIG. 1: Oligonucleotide primers for PCR detection of ORF 1, 2, 6, 7-10.

FIG. 2: Putative function of the genes present on the *B. hyodysenteriae* plasmid.

FIG. 3: Oligonucleotide primers for PCR detection of ORF 11-16.

FIG. 4: Comparison of the plasmid gene content of virulent and avirulent strains of *B. hyodysenteriae* using microarray-based comparative genomic hybridisation and PCR analysis (*=PCR analysis). Genes that are absent in different strains are shaded. The box indicates the six genes (ORF 11-16) associated with LPS biosynthesis which are present in the virulent strains but absent in the avirulent strains (P=present; A=absent).

DETAILED DESCRIPTION

Figure 5:
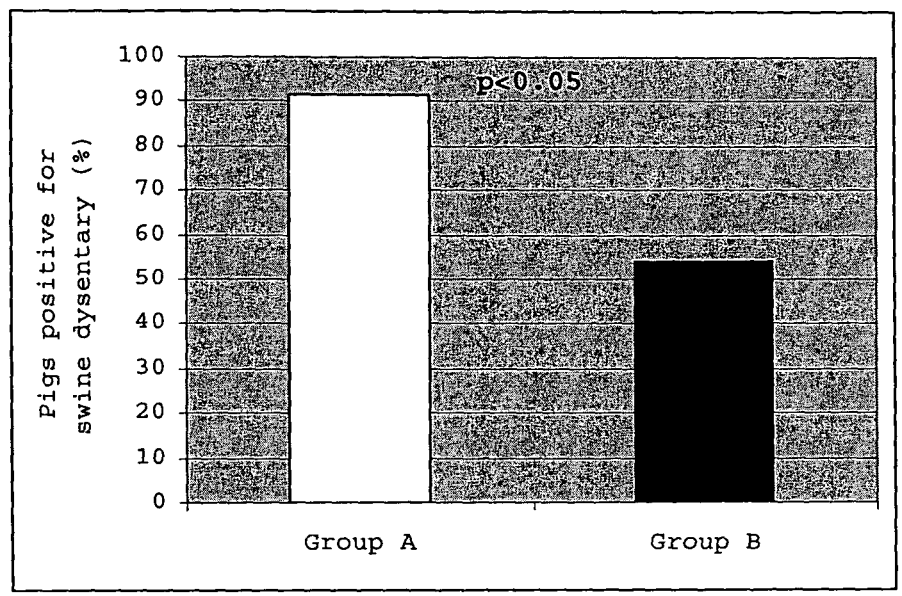
FIG. 5: Percentage of pigs positive for *B. hyodysenteriae* infection and for symptoms of swine dysentery after infection with virulent *B. hyodysenteriae* strain WA1 (Group A) or an uncharacterised field strain of *B. hyodysenteriae* that did not contain the virulence factors encoded by ORFs 11-16 (Group B).

Before describing the present invention in detail, it is to be understood that this invention is not limited to particularly exemplified methods and may, of course, vary.

It is also to be understood that the terminology used herein is for the purpose of describing particular embodiments of the invention only, and is not intended to be limiting which will be limited only by the appended claims.

All publications, patents and patent applications cited herein, whether supra or infra, are hereby incorporated by reference in their entirety. However, publications mentioned herein are cited for the purpose of describing and disclosing the protocols, reagents and vectors which are reported in the publications and which might be used in connection with the invention. Nothing herein is to be construed as an admission that the invention is not entitled to antedate such disclosure by virtue of prior invention.

Furthermore, the practice of the present invention employs, unless otherwise indicated, conventional immunological and molecular biological techniques and pharmacology within the skill of the art. Such techniques are well known to the skilled worker, and are explained fully in the literature. See, eg., Coligan, Dunn, Ploegh, Speicher and Wingfield "Current protocols in Protein Science" (1999) Volume I and II (John Wiley & Sons Inc.); Sambrook et al., "Molecular Cloning: A Laboratory Manual" (1989), $2^{nd}$ Edition (Cold Spring Harbor Laboratory press); and Prescott, Harley and Klein "Microbiology" (1999), $4^{th}$ Edition (WBC McGraw-Hill).

It must be noted that as used herein and in the appended claims, the singular forms "a," "an," and "the" include plural reference unless the context clearly dictates otherwise. Thus, for example, a reference to "a gene" includes a plurality of such genes, and a reference to "an animal" is a reference to one or more animals, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

In the broadest aspect of the invention there is provided a vaccine strain of *B. hyodysenteriae*. *B. hyodysenteriae* are anaerobic, gram-negative, chemotrophic bacteria belonging to the class Spirochaetae and are characterised by their long, slender, helical shape. Animals infected by *B. hyodysenteriae* develop diarrhoeal diseases. Porcine animals infected by *B. hyodysenteriae* develop swine dysentery characterised by extensive inflammation and necrosis of the epithelial surface of the large intestine. Accordingly, while it is particularly contemplated that the vaccines, compounds and methods of the invention are suitable for use in porcine animals (pigs and hogs), they are also applicable to other mammalian and avian species of animal, including humans, companion animals such as dogs and cats, and domestic animals such as chicken and geese, horses, cattle and sheep, or zoo mammals such as non-human primates, felids, canids and bovids.

The vaccine strain of the present invention is a live strain of *B. hyodysenteriae*. The term "strain", as used herein, describes variants of a bacterial species that can be distinguished by one or more characteristics, such as ribosomal RNA sequence variation, DNA polymorphisms, serological typing, or toxin production, from other strains within that species. In the present invention *B. hyodysenteriae* strains are distinguished by their virulence status, i.e. strains are classified as virulent or avirulent. Examples of virulent *B. hyodysenteriae* strains include WA1, B204, Vic2, BW1, NSW5, Q17, NSW15, while examples of avirulent strains include B78$^T$, SA2206, VS1, B234, R301, B6933, FM 88.90 and A1.

In some embodiments, the vaccine strain is an attenuated virulent strain. The terms "virulent", "virulence", or grammatical equivalents thereof, are used herein to describe *B. hyodysenteriae* strains with the ability to cause the clinical symptoms associated with diarrhoeal diseases.

The virulent characteristics of a virulent strain result from its production of virulence factors. The term "virulence factor", as used herein, relates to products that contribute to the virulence of *B. hyodysenteriae* or the ability of *B. hyodysenteriae* to cause disease. Virulence factors may be proteins or carbohydrates and include coagulases, collagenases, hemolysins and lipopolysaccharides. For example, products are associated with rhamnose biosynthesis may also be virulence factors. Lipopolysaccharide (LPS) consists of three distinct structural domains: lipid A, the core, and the O-antigen. Lipid A functions as a hydrophobic membrane anchor and forms the bioactive component of the molecule. The core region consists of a complex oligosaccharide, which, as compared to the O-antigen, shows only limited structural variability. The O-antigen comprises the most variable part of the LPS and confers bacteria serotype specificity. It is composed of repeating sugar subunits of one to eight sugars. Each O-chain can contain up to 50 of these subunits. Rhamnose is an important moiety in the O-specific antigen of LPS comprising the cell wall and in the capsule of many pathogenic bacteria. The cell wall and capsule interact with the host during infection and are vital for bacterial survival. A loss of the carbohydrate portion in LPS leads to strains with rough colony morphology. Typically, the virulence of rough strains is strongly reduced and their sensitivity towards antibiotics or serum components is increased.

Accordingly, in some embodiments the virulence factors of the present invention encode products that are associated with rhamnose biosynthesis.

In some embodiments, the virulence factors are encoded by one or more polynucleotide sequences substantially similar to one or more of the nucleic acid sequences depicted in SEQ ID NO:1, SEQ ID NO:2, SEQ ID NO:3, SEQ ID NO:4, SEQ ID NO:5 or SEQ ID NO:6 or functional variants thereof. The terms "nucleic acid", "polynucleic acid" or "polynucleotide" refer herein to deoxyribonucleic acid and ribonucleic acid in all their forms, i.e., single and double-stranded DNA, cDNA, mRNA, and the like.

As used herein, the term "substantially similar" refers to equivalent nucleotide sequences to those depicted in SEQ ID NO:1, SEQ ID NO:2, SEQ ID NO:3, SEQ ID NO:4, SEQ ID NO:5 or SEQ ID NO:6 but differ by one or more nucleotide substitutions, additions or deletions, such as allelic variants, and will also include sequences that differ due to the degeneracy of the genetic code. Equivalents will also include nucleotide sequences that are "substantially homologous" ie at least about 85%, preferably at least about 90%, and most preferably at least about 95%, of the nucleotides match over the defined length of the nucleotide sequences. Sequences that are substantially similar can be identified in a Southern hybridisation experiment, for example under high, medium or low stringency conditions as defined for that particular system.

As used herein, the term "encode" in its various grammatical forms includes nucleotides and/or amino acids that correspond to other nucleotides or amino acids in the transcriptional and/or translational sense.

A "double-stranded DNA molecule" refers to the polymeric form of deoxyribonucleotides (adenine, guanine, thymine, or cytosine) in its normal, double-stranded helix.

This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the non-transcribed stand of DNA (i.e., the strand having a sequence homologous to the mRNA).

A DNA sequence "corresponds" to an amino acid sequence if translation of the DNA sequence in accordance with the genetic code yields the amino acid sequence (i.e., the DNA sequence "encodes" the amino acid sequence). One DNA sequence "corresponds" to another DNA is sequence if the two sequences encode the same amino acid sequence. A DNA sequence is a "functional variant" of another DNA sequence when at least about 85%, preferably at least about 90%, and most preferably at least about 95%, of the nucleotides match over the defined length of the DNA sequences and the corresponding activity of the proteins encoded by the DNA sequences is equivalent. A length of DNA sequence that encodes a protein may be referred to as a "gene".

The term "attenuated" is used herein to describe a virulent strain of *B. hyodysenteriae* that has been modified so that it is no longer capable of causing disease (i.e., the modified strain is avirulent).

The term "live" is used herein to describe *B. hyodysenteriae* that are able to grow and reproduce. Accordingly, the live *B. hyodysenteriae* strain of the present invention should be able to colonise the colon of an animal but not cause the clinical symptoms associated with diarrhoeal diseases caused by *B. hyodysenteriae* infection. Further, the live strain of the present invention should be capable of limited replication in the vaccinated animal and of inducing a protective immune response which is protective against virulent strains of *B. hyodysenteriae*.

A virulent *B. hyodysenteriae* strain as described herein may be a clinically known virulent strain or a strain that is identified as containing virulence factors. Accordingly, the present invention also provides methods of identifying virulent *B. hyodysenteriae* strains. For example, a first step in identifying if a *B. hyodysenteriae* strain is a virulent strain is to determine the presence or absence of virulence factors in the strain. In some embodiments, these virulence factors are encoded by one or more polynucleotide sequences substantially similar to one or more of the nucleic acid sequences depicted in SEQ ID NO:1, SEQ ID NO:2, SEQ ID NO:3, SEQ ID NO:4, SEQ ID NO:5, or SEQ ID NO:6 or functional equivalents thereof. The presence of a polynucleotide or gene encoding these virulence factors may be determined by the analysis of any factors associated with or indicative of transcription and/or translation of the polynucleotide or gene including, but not limited to, RNA expression levels and protein expression levels, as well as the presence of the DNA sequence within the chromosome or cytoplasm. Techniques for identifying the presence of a polynucleotide or gene or its product in a sample are well known by one skilled in the art and described elsewhere herein. In some embodiments, the presence of one or more virulence factors in the unknown strain will indicate that it is a virulent strain.

Once obtained, the virulent *B. hyodysenteriae* strain may be modified by any of a number of methods known in the art including, but not limited to, multiple serial passage, temperature sensitive attenuation, mutation, or the like such that the resultant strain is attenuated ie avirulent and not capable of causing disease in an animal.

In some embodiments, the modification to the virulent strain results in the reduction or suppression of expression of polynucleotides or genes encoding virulence factors or leads to the expression of non-functional virulence factors.

There are a number of techniques well known in the art for reducing or abolishing polynucleotide expression. For example, a mutation may be introduced at a predetermined site, such as the promoter region or within the coding sequence to produce a nonsense mutation, using recombinant DNA-technology. Recombinant DNA techniques comprise cloning the gene of interest, modification of the gene sequence by site-directed mutagenesis, restriction enzyme digestion followed by re-ligation and subsequent replacement of the wild type gene with the mutant gene.

Standard recombinant DNA techniques such as cloning the virulence factor gene into a plasmid, digestion of the polynucleotide sequence with a restriction enzyme, followed by endonuclease treatment, re-ligation and homologous recombination in the host strain, are all known in the art and described inter alia in Sambrook et al., "Molecular Cloning: A Laboratory Manual" (1989), $2^{nd}$ Edition (Cold Spring Harbor Laboratory press). Site-directed mutations can, for example, be made by means of in vitro site directed mutagenesis using the TRANSFORMER® kit sold by Clontech. PCR-techniques are extensively described in Dieffenbach & Dreksler (1995) "PCR Primer—A Laboratory Manual" (Cold Spring Harbour Laboratory Press) and elsewhere herein.

In some embodiments, a mutation may be introduced at a predetermined site in chromosomal or extrachromosomal DNA (eg. a plasmid) via an insertion, a deletion, or a substitution of one nucleotide by another, such as a point mutation, which leads to a mutated gene that has reduced or no expression. The mutation should produce a *B. hyodysenteriae* strain that has a reduced capacity to cause diarrhoeal diseases, such as swine dysentery. Preferably, the mutation is a deletion mutation, where disruption of the gene is caused by the excision of nucleic acids. Such a mutation can, for example, be made by the deletion of a contiguous span of base pairs. Even very small deletions such as stretches of 10 base pairs can cause the gene to encode no protein or a non-functional protein. Even the deletion of one single base pair may lead to no protein or a non-functional protein, since as a result of such a mutation, the other base pairs are no longer in the correct reading frame or transcription has been inhibited or diminished. More preferably, a longer stretch is removed e.g. 100 base pairs. Even more preferably, the whole gene is deleted.

Well-defined and deliberately made mutations involving the deletion of fragments or the whole gene, or combinations thereof, have the advantage, in comparison to classically induced mutations, that they will not revert to wild-type. Thus, in some embodiments of the invention the vaccine strain comprises a live attenuated virulent *B. hyodysenteriae* strain in which a mutation in a gene encoding a virulence factor comprises a deletion or an insertion to disrupt the polynucleotide sequence encoding the virulence factor so that no corresponding protein is produced or the protein is non-functional.

One skilled in the art will also appreciate that having identified the virulence factors of *B. hyodysenteriae* it would be possible, using no more than the techniques described herein, to identify naturally occurring strains of *B. hyodysenteriae* that are avirulent or comprise one or more preexisting mutations in a polynucleotide or gene encoding a virulence factor which can be used as live vaccine strains. These naturally occurring *B. hyodysenteriae*, once isolated by standard techniques, can, if required, be subjected to further mutagenesis or recombinant DNA techniques to construct a double or multiple mutant strain. Further, the *B. hyodysenteriae* strain may contain deletions of whole genes encoding virulence factors. In some embodiments, the *B. hyodysenteriae* strain will be a wild-type avirulent strain that has preexisting deletion mutations in all virulence genes.

Techniques for identifying bacteria that have one or more mutations in genes encoding virulence factors are known by one skilled in the art. Accordingly, routine techniques for the detection of *B. hyodysenteriae* strains that have been mutated by the techniques described above include Northern and Western blotting, PCR, ELISAs and cytotoxicity assays as described elsewhere herein. Mutant strains with no functional genes encoding virulence factors can easily be selected as described elsewhere herein.

Genes encoding the virulence factors of the present invention may be plasmid-borne. Therefore, in some embodiments the modification to a virulent *B. hyodysenteriae* strain comprises curing the strain of one or more plasmids. The term "plasmid", as herein used, refers to cytoplasmic DNA that replicates independently of the bacterial chromosome. A variety of methods involving chemical and physical agents have been developed for eliminating or "curing" plasmids from a bacterial strain. The curing of a bacterial strain of a plasmid does not involve the physical removal of the plasmid directly, but instead concerns interfering with the replication and/or partitioning of the plasmid so as to increase the rate at which plasmid-free partitions occur.

Standard protocols for curing plasmids such as exposure of a bacterial culture to sub-inhibitory concentrations of some chemical agents, e.g. acridine orange, acriflavine, sodium dodecyl sulfate or to a super-optimal temperature followed by selection of cured derivatives, are all known in the art and described inter alia in Sambrook et al., "Molecular Cloning: A Laboratory Manual" (1989), $2^{nd}$ Edition (Cold Spring Harbor Laboratory press). Plasmids can be cured from a strain, for example, by exposure of is the culture to ethidium bromide. In one example, *B. hyodysenteriae* cells can be grown to mid-log phase in anaerobic trypticase soy broth culture. The cells are then serially diluted in, for example, anaerobic trypticase soy broth containing about 30 µg/ml of ethidium bromide and maintained at about 37° C. under anaerobic conditions with shaking for about 3 days. The viable culture from the highest serial dilution is serially diluted in anaerobic trypticase soy broth culture containing 30 µg/ml of ethidium bromide and maintained at 37° C. under the same conditions for 3 days. This process is repeated at least another nine times and following the final passage the bacterial cells are washed to remove the ethidium bromide and plated onto an agar medium such as Fastidious Anaerobic Agar (LabM) plates to obtain single colonies.

Techniques for identifying cured derivatives are known by one skilled in the art. Routine techniques for their detection such as Northern and Western blotting, ELISAs and cytotoxicity assays are known in the art. In one example, the single colonies are screened for the loss of a plasmid by PCR. The absence of PCR product for all virulence factors, compared with the presence of all the products in the wild-type *B. hyodysenteriae* strain is indicative of successful plasmid curing.

It would be apparent to one of skill in the art that these same techniques could be applied to identify naturally occurring avirulent strains of *B. hyodysenteriae* that lack one or more plasmids containing virulence genes.

"Polymerase chain reaction" or "PCR", as used herein, generally refers to a method for amplification of a desired nucleotide sequence in vitro. In general, the PCR method involves repeated cycles of primer extension synthesis in the presence of PCR reagents, using two oligonucleotide primers capable of hybridizing preferentially to a template nucleic acid. Typically, the primers used in the PCR method will be complementary to nucleotide sequences within the template at both ends of or flanking the nucleotide sequence to be amplified, although primers complementary to the nucleotide sequence to be amplified also may be used. In some embodiments the PCR primers used to identify the presence of genes encoding virulence factors are those set out in FIG. 3.

PCR may also be used to determine whether a specific sequence is present, by using a primer that will specifically bind to the desired sequence, where the presence of an amplification product is indicative that a specific binding complex was formed. Alternatively, the amplified sample can be fractionated by electrophoresis, e.g. capillary or gel electrophoresis, transferred to a suitable support, e.g. nitrocellulose, and then probed with a fragment of the template sequence.

"Oligonucleotides primers", "oligonucleotides probes" or "PCR primers" are short-length, single- or double-stranded polydeoxynucleotides that are chemically synthesised by known methods (involving, for example, triester, phosphoramidite, or phosphonate chemistry). Typically they are then purified, for example, by polyacrylamide gel electrophoresis. Primers and probes of the invention are DNA molecules that are sufficiently complementary to regions of contiguous nucleic acid residues within the gene nucleic acid encoding a virulence factor to hybridise thereto, preferably under high stringency conditions. Defining appropriate hybridisation conditions is within the skill of the art. However, briefly, "stringent conditions" for hybridisation or annealing of nucleic acid molecules are those that (1) employ low ionic strength and high temperature for washing, for example, 0.015M NaCl/0.0015M sodium citrate/0.1% sodium dodecyl sulfate (SDS) at 50° C., or (2) employ during hybridisation a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75M NaCl, 0.075M sodium citrate), 50 mM sodium phosphate (pH 6.8), 0.1% sodium pyrophosphate, 5×Denhardt's solution, sonicated salmon sperm DNA (50 µg/mL), 0.1% SDS, and 10% dextran sulfate at 42° C., with washes at 42° C. in 0.2×SSC and 0.1% SDS.

Exemplary primers and probes include oligonucleotides that are at least about 15 nucleic acid residues long and that are selected from any 15 or more contiguous residues of DNA. Preferably, oligonucleotides primers and probes used in some embodiments of the invention are at least about 20 nucleic acid residues long. The invention also contemplates oligonucleotide primers and probes that are 150 nucleic acid residues long or longer. Those of ordinary skill in the art realise that nucleic hybridisation conditions for achieving the hybridisation of a primer or probe of a particular length to a nucleic acid molecule of the invention can readily be determined. Such manipulations to achieve optimal hybridisation conditions for probes of varying lengths are well known in the art. In some embodiments the oligonucleotide primers used to identify the presence of genes encoding virulence factors are set out in FIG. 3.

As used herein, the term "PCR reagents" refers to the chemicals, apart from the template nucleic acid sequence, needed to perform the PCR process. These chemicals generally consist of five classes of components: (i) an aqueous buffer, (ii) a water soluble magnesium salt, (iii) at least four deoxyribonucleotide triphosphates (dNTPs), (iv) oligonucleotide primers (normally two primers for each template sequence, the sequences defining the 5' ends of the two complementary strands of the double-stranded template sequence), and (v) a polynucleotide polymerase, preferably a DNA polymerase, more preferably a thermostable DNA polymerase, ie a DNA polymerase which can tolerate temperatures between 90° C. and 100° C. for a total time of at least 10 minutes without losing more than about half its activity. An example of a suitable polynucleotide polymerase is HotStarTaq DNA Polymerase (Qiagen).

The four conventional dNTPs are thymidine triphosphate (dTTP), deoxyadenosine triphosphate (dATP), deoxycitidine triphosphate (dCTP), and deoxyguanosine triphosphate (dGTP). These conventional deoxyribonucleotide triphosphates may be supplemented or replaced by dNTPs containing base analogues which Watson-Crick base pair like the conventional four bases, e.g. deoxyuridine triphosphate (dUTP).

A detectable label may be included in an amplification reaction. Biotin-labelled nucleotides can be incorporated into DNA or RNA by such techniques as nick translation, chemical and enzymatic means, and the like. The biotinylated primers and probes are detected after hybridisation, using indicating means such as avidin/streptavidin, fluorescent-labelling agents, enzymes, colloidal gold conjugates, and the like. Nucleic acids may also be labelled with other fluorescent compounds, with immunodetectable fluorescent derivatives, with biotin analogues, and the like. Nucleic acids may also be labelled by means of attachment to a protein. Nucleic acids cross-linked to radioactive or fluorescent histone single-stranded binding protein may also be used. Those of ordinary skill in the art will recognise that there are other suitable methods for detecting oligonucleotide primers and probes and other suitable detectable labels that are available for use in the practice of the present invention. Moreover, fluorescent residues can be incorporated into oligonucleotides during chemical synthesis. Preferably, oligonucleotides primers and probes of the invention are labelled to render them readily detectable. Detectable labels may be any species or moiety that may be detected either visually or with the aid of an instrument.

Suitable labels include fluorochromes, eg. fluorescein isothiocyanate (FITC), rhodamine, Texas Red, phycoerythrin, allophycocyanin, 6-carboxyfluorexcein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, eg. $^{32}$P, $^{35}$S, $^{3}$H, as well as others. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-touidinyl-6-naphthalene sulfonate. Other dyes include 3-phenyl-7-isocyanatocoumarin, acridines, such as 9-isothiocyanatoacridine acridine orange; N-(p-(2-benzoaxazolyl)phenyl)maleimide; benzoxadiazoles, stilbenes, pyrenes, and the like. Most preferably, the fluorescent compounds are selected from the group consisting of VIC, carboxy fluorescein (FAM), Lightcycler® 640, and Cy5.

The label may be a two stage system, where the amplified DNA is conjugated to biotin, haptens, or the like having a high affinity binding partner, e.g. avidin, specific antibodies, etc, where the binding partner is conjugated to a detectable label. The label may be conjugated to one or both of the primers.

Alternatively, the pool of nucleotides used in the amplification is labelled, so as to incorporate the label into the amplification product.

The vaccine strain of the present invention should retain its immunogenic properties and be protectively immunogenic. The term "immunogenic properties" as used herein, refers to the ability of the vaccine strain to generate in an animal the development of a humoral and/or a cellular immune response to an antigen. For purposes of the present invention, a "humoral immune response" refers to an immune response mediated by antibody molecules, while a "cellular immune response" is one mediated by T-lymphocytes and/or other white blood cells.

One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, non-specific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition or vaccine that elicits a cellular immune response may serve to sensitize a subject by the presentation of antigen in association with MHC molecules at the cell surface. The cell-mediated immune response is directed at, or near, cells presenting antigen at their is surface. In addition, antigen-specific T-lymphocytes can be generated to allow for the future protection of an immunized host.

The ability of a particular immunogen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. Methods of measuring cell-mediated immune response include measurement of intracellular cytokines or cytokine secretion by T-cell populations, or by measurement of epitope specific T-cells.

Thus, the term "immunogenic properties", as used herein, may be one that stimulates the production of antibodies or elicit the production of CTLs. Hence, the immunogenic properties of the vaccine strain of the present invention may initiate one or more of the following effects: the production of antibodies by B-cells; and/or the activation of suppressor T-cells directed specifically to an antigen or antigens present in the vaccine composition of the present invention. These responses may serve to neutralize infectivity and prevent colonisation of the bacteria in the intestine, and/or mediate antibody-complement, or antibody dependent cell cytotoxicity (ADCC) to provide protection to an immunized host. Accordingly, the immunogenic properties of the vaccine strain are "protectively immunogenic".

In some embodiments, the method of preparing a vaccine strain not only comprises the steps of selecting a virulent strain and producing a modification in the virulent strain, but also the steps of isolating and selecting the live attenuated virulent *B. hyodysenteriae* strain that contains the modification. Methods of isolating and selecting modified strains of *B. hyodysenteriae* are known in the art and described elsewhere herein.

Once produced the vaccine strain of the present invention may be administered to an animal to prevent dysentery caused by *B. hyodysenteriae* colonisation. In some embodiments, an animal is administered with an effective amount of at least one vaccine strain of *B. hyodysenteriae*.

The vaccine strains of the present invention can be administered in dosages and by techniques well known to those skilled in the medical or veterinary arts, taking into consideration such factors as the age, sex, weight, species and condition of the recipient animal, and the route of administration. The route of administration can be percutaneous, via mucosal administration (e.g., oral, nasal, anal, vaginal) or via a parenteral route (intradermal, intramuscular, subcutaneous, intravenous, or intraperitoneal). Vaccine strains can be administered alone, or can be co-administered or sequentially administered with other treatments or therapies. Forms of administration may include suspensions, syrups or elixirs, and preparations for parenteral, subcutaneous, intradermal, intramuscular or intravenous administration (e.g., injectable administration) such as sterile suspensions or emulsions.

Vaccine strains may be administered as a spray or mixed in food and/or water or delivered in admixture with a suitable carrier, diluent, adjuvant or excipient such as sterile water, physiological saline, glucose, or the like. The vaccine strains may contain auxiliary substances such as wetting or emulsifying agents, pH buffering agents, adjuvants, gelling or viscosity enhancing additives, preservatives, flavoring agents, colours, and the like, depending upon the route of administration and the preparation desired. Standard pharmaceutical texts, such as "Remington's Pharmaceutical Sciences" (1990), 18$^{th}$ Edition (Mack Publishing Co.), may be consulted to prepare suitable preparations without undue experimentation.

The vaccine strain of the present invention may also be used in the preparation of a vaccine composition. In some embodiments that vaccine composition comprises at least one of the vaccine strains of *B. hyodysenteriae* described herein in a pharmaceutically acceptable vehicle. The present invention also provides in some embodiments the use of a vaccine strain of *B. hyodysenteriae* in the manufacture of a medicament used to prevent *B. hyodysenteriae* infection. Pharmaceutical carriers for preparation of pharmaceutical compositions and medicaments are well known in the art, as set out in textbooks such as "Remington's Pharmaceutical Sciences" (1990), 18$^{th}$ Edition (Mack Publishing Co.). Methods of administering vaccine compositions are also known in the art and described above.

The present invention also provides in some embodiments a method of vaccination against *B. hyodysenteriae* infection by administering an effective amount of the vaccine composition. Logically, the present invention also provides a method of conferring immunity to an animal, such as a swine, against *B. hyodysenteriae* infection by administering to the animal an effective amount of the vaccine composition described above.

The compositions as disclosed in the embodiments of the invention may be part of a kit. Typically the kit would also include instructions for use.

The present invention also relates to a method of diagnosing virulent *B. hyodysenteriae* colonisation in an is animal. In some embodiments the method comprises obtaining a sample from an animal suspected of having a *B. hyodysenteriae* infection.

A "sample" refers to animal tissue, biological fluids or other materials suspected of containing *B. hyodysenteriae*, or its polynucleotides or its polypeptides. Examples of such tissues, fluids or materials include, but not limited to, plasma, serum, faecal material, urine, biopsy material including stomach and intestine samples. The sample might also include in vitro cell culture constituents.

Whether an animal is colonised with a virulent strain of *B. hyodysenteriae* may be determined by assessing the presence or absence of polynucleotides or genes encoding virulence factors as discussed supra. The presence of a gene may be determined by the analysis of any factors associated with or indicative of transcription and translation of a gene including, but not limited to RNA expression levels and protein expression levels, as well as the presence of the DNA sequence within the chromosome or extrachromosomally.

Techniques for identifying the presence of a gene or its product in a sample are known by one skilled in the art. Routine techniques such as Northern and Western blotting, PCR, microarrays and ELISAs are known in the art and described elsewhere herein. In one embodiment the presence of genes encoding virulence factors within a strain may be determined by ELISA. Protocols upon which ELISA assays may be based include for example competition assays, direct reaction assays and sandwich type assays. In ELISA assays samples including, for example, biological fluids and tissue samples may be added to peptide coated wells in, for example, a microtitre tray where an immunological complex forms if antibodies are present in the sample. A signal generating means may be added to detect complex formation. A detectable signal is produced if specific antibodies are present in the sample.

For example, microtitre plates may be are coated with *B. hyodysenteriae* peptides corresponding to virulence factors in, for example, a carbonate buffer. Coating is allowed to occur in a humidified chamber at about 4° C. overnight. Plates may be blocked with PBS-BSA with mixing and washed with PBST. Diluted pig sera are added to the plates and incubated. Plates may then be washed before adding, for example, goat anti-pig IgG-HRP. K-Blue TMB substrate can then be added and colour development allowed to occur before being stopped with the addition of sulphuric acid. The optical density of each well can then be read. The existence of colour in this example would indicated that antibodies specific for *B. hyodysenteriae* virulence factors are present in the sample and as such the animal is colonised with a virulent strain of *B. hyodysenteriae*.

A point of care device in the form of a flow through test may also be used to diagnose whether an animal is colonised with a virulent strain of *B. hyodysenteriae*. In a flow through test, a biological sample is added to a nitrocellulose membrane on which antibodies to virulence factors are immobilized, and when a sample passes through the membrane, polypeptides bind to the immobilized antibodies to form immune complexes. When a solution including labelled secondary antibodies passes through the membrane, it binds to the immune complexes. In a strip test, once a biological sample is added, the biological sample passes through a region including labelled antibodies, and polypeptides bind to labelled antibodies to form immune complexes.

When a biological sample passes through a region including a solid phase antibody, polypeptides bind to the immune complexes. The quantity of secondary antibodies detected in the region with immobilized antibodies shows the presence or absence of virulence factors in the sample.

The present invention also relates to a method of screening for compounds capable of modulating the virulence of a *B.*

*hyodysenteriae* strain. In some embodiments the method of screening evaluates the potential of compounds to modulate the expression or target the activity of *B. hyodysenteriae* virulence factors.

The term "compounds" preferably includes, but is not limited to, small organic molecules, peptides, polypeptides and antibodies that bind to a polynucleotide and/or polypeptide encoding a virulence factor, such that the activity or expression of the virulence factor or target thereof is inhibited or suppressed. Potential compounds may be small organic molecules, a peptide, a polypeptide, such as a closely related protein, or an antibody that binds the same site(s) on a binding molecule.

The term "compounds" also potentially includes small molecules that bind to and occupy the binding site of a virulence factor polypeptide, thereby preventing binding to cellular binding molecules, such that normal biological activity is prevented. Examples of small molecules include but are not limited to small organic molecules, peptides or peptide-like molecules. Other examples of potential polypeptide antagonists include antibodies or, in some cases, oligonucleotides or proteins which are closely related to the ligands, substrates, receptors, enzymes, etc., as the case may be, of the polypeptide, e.g., a fragment of a ligand, substrate, receptor, enzyme, etc.; or small molecules which bind to the polypeptide of the present invention but do not elicit a response, so that the activity of the polypeptide is prevented. Other potential compounds include antisense molecules, see, for example, "Oligodeoxynucleotides as Antisense Inhibitors of Gene Expression" (1988) CRC Press, for a description of these molecules.

In some embodiments, it may be desirable to immobilize either the polypeptides encoding virulence factors or their target molecules or ligands, to accommodate automation of the assay. Binding of a test compound to a protein encoding a virulence factor (or fragment, or variant thereof) or interaction of such a protein with a target molecule or ligand in the presence and absence of a candidate compound, can be accomplished in any vessel suitable for containing the reactants.

Examples of such vessels include microtitre plates, test tubes and micro-centrifuge tubes.

In some embodiments a fusion protein can be provided which adds a domain that allows one or both of the proteins to be bound to a matrix. Techniques for immobilizing proteins on matrices are well-known in the art.

In some embodiments the method comprises the use of a DNA construct that codes for a reporter gene under the control of a transcriptional regulatory sequence or a promoter of a gene encoded by a polynucleotide sequence depicted in SEQ ID NO:1, SEQ ID NO:2, SEQ ID NO:3, SEQ ID NO:4, SEQ ID NO:5 or SEQ ID NO:6. Cells containing the construct are contacted with a compound to be tested and the amount of signal produced by the reporter gene measured. If the amount of reporter gene product produced is less than that produced by control cells not exposed to the compound, the compound is capable of inhibiting *B. hyodysenteriae* virulence.

The invention will now be further described by way of reference only to the following non-limiting examples. It should be understood, however, that the examples following are illustrative only, and should not be taken in anyway as a restriction on the generality of the invention described above.

Example 1

Genome Sequencing

An Australian porcine field isolate of *B. hyodysenteriae* (strain WA1) was shotgun sequenced. This strain has been well-characterised and shown to be virulent following experimental challenge of pigs. The spirochaete was grown in anaerobic trypticase soy broth culture and 100 μg DNA was extracted using a cetyltrimethylammonium bromide (CTAB) method to prepare high quality high molecular weight DNA suitable for preparation of genomic DNA libraries. The genomic DNA was sheared using a GeneMachines Hydroshear, and the fragmented DNA processed for cloning as per the protocol recommended by the suppliers of the pSMART vector system (Lucigen). A small insert (2-3 kb) library and a medium insert (3-10 kb) library are constructed into the low copy version of the pSMART vector and random clones are sequenced using the AB 3730 DNA sequencer to provide at least 8× coverage of the genome. To further close the genome sequence, shotgun libraries for the Roche GS-FLX were prepared from the genomic DNA with an average insert size of 500 bp. Random clones from this library were sequenced using the Roche GS-FLX DNA sequencer. Finally, primer walking between un-linked contiguous sequences was used to finish the genome sequence.

Example 2

Annotation

All genome sequences for *B. hyodysenteriae* were assembled and annotated by the Australian Genome Research Facility (AGRF) in Queensland and at Murdoch University by the Centre for Comparative Genomics (CCG). A range of public domain bioinformatics tools were used to analyse and re-analyse the sequences as part of a quality assurance procedure on data analysis. Open reading frames (ORFs) were predicted using a variety of programs including GeneMark, GLIMMER, ORPHEUS, SELFID and GetORF. Putative ORFs are examined for homology (DNA and protein) with existing international databases using searches including BLAST and FASTA. Phylogenetic and other molecular evolution analyses were conducted with the identified genes and with other species to assist in the assignment of function. The in silico analysis of the partially sequenced genome produced a comprehensive list of all the predicted ORFs present in the sequence data available.

The combination of data from the different sequencing platforms for the *B. hyodysenteriae* genome results in the identification of a 3,000,694 bp genome and a 35,940 bp circular extra-chromosomal plasmid. The genome was predicted to encode 2,551 ORFs and the plasmid encodes 32 ORFs. Comparison of the predicted ORFs with genes present in the nucleic acid and protein databases indicates that approximately 70% of the predicted ORFs had homology with genes contained in the databases. The remaining 30% of the ORFs have no known identity. The putative functions of the 32 predicted genes present on the plasmid are shown in FIG. 2. The majority of these genes have functions associated with cell-envelope biosynthesis, and specifically, lipopolysaccharide (LPS) biosynthesis.

Example 3

Microarray Analysis and PCR Analysis

Custom GeneChips are designed and manufactured by Affymetrix using the predicted ORFs from the *B. hyodysenteriae* genome and plasmid sequence. Of the 2,551 ORFs encoded on the genome, 1718 genes are represented on the GeneChip, and 25 out of the 32 ORFs encoded on the plasmid are represented on the chip. Microarray-based comparative genomic hybridisation (CGH) analysis was used to compare the gene content of six highly virulent *B. hyodysenteriae* strains (strains B204, BW1, Vic2, NSW5, NSW15 and Q17) and eight low virulence strains (strains B234, SA2206, VS1, A1, B78$^T$, R301, B6933 and FM88.90) with the gene content of *B. hyodysenteriae* strain WA1, also a highly virulent strain. The virulent strains have been reported to cause severe clinical signs of SD in experimentally and naturally infected pigs. The avirulent strains have been reported to colonise pigs without causing significant clinical signs of SD. High molecular weight DNA was extracted from the *B. hyodysenteriae* cells using the DNeasy Blood and Tissue Kit (Qiagen) according to the manufacturer's instructions. The purified high molecular weight DNA was digested with restriction enzyme Rsal and the resulting restriction fragments labelled with a fluorescent cyanide dye (Cy3) using the BioPrime Array CGH Genomic Labelling System (Invitrogen) according to the manufacturer's instructions. The labelled genome fragments were hybridised to the *B. hyodysenteriae* Gene-Chip under moderately stringent conditions (37° C.) in the Hybridisation Oven 645 (Affymetrix) for 16 hours. The GeneChips were washed and labelled using the GeneChip Hybridisation, Wash and Stain Kit (Affymetrix) according to the manufacturer's instructions. The Fluidics Station 450 (Affymetrix) was used to perform the washing and staining of the GeneChips. Finally, the hybridised GeneChip was scanned using the Scanner 3000 (Affymetrix) and the composite image analysed using the GeneChip Operating Software (GCOS, Affymetrix).

For the seven plasmid ORFs not represented by the Gene-Chip, three unique primer pairs were designed for the PCR amplification of each ORF (Table 1). High molecular weight DNA from all the strains used in the CGH microarray analysis was subjected to polymerase chain reaction (PCR) using Hot-StarTaq DNA Polymerase (Qiagen) according to the manufacturer's instructions. The annealing temperature used for each primer was set at 5° C. less than the optimal annealing temperature to allow for a moderate stringency similar to that of the microarray hybridisation. The amplification products were electrophoreses through an agarose gel, stained with ethidium bromide and viewed over ultraviolet light. The presence of one or more products for an ORF was indicative of the presence of that ORF on the plasmid.

The comparison of the plasmid gene content of the virulent and avirulent strains are shown in FIG. 4. These results indicate that all strains analysed possess the plasmid, except avirulent strains A1 and FM88.90. For the strains which possessed the plasmid, ORFs 1-10, 17-24 and 26-32 are present on all plasmids. The distribution of ORF 25 was variable amongst the strains and does not correlate with their virulence. ORFs 11-16 were present on the plasmid of the virulent strains but were absent on the plasmid of the avirulent strains. These results indicate that ORFs 11-16 encode virulence factors.

Accordingly, strains without the identified functional virulence factors would be useful as live vaccine strains. Additionally, the detection of ORFs 11-16 in a strain of unknown virulence would provide a useful means of determining whether the strain was virulent. Similarly, assessing the presence of the identified virulence factors could be used to diagnose whether or not a subject is infected with a virulent strain of *B. hyodysenteriae*.

Example 4

Elimination of Plasmid ("Curing")

*B. hyodysenteriae* strain WA1 cells were grown to mid-log phase in anaerobic trypticase soy broth culture. The cells were serially diluted in anaerobic trypticase soy broth containing 30 μg/ml of ethidium bromide and maintained at 37° C. under anaerobic conditions with shaking for 3 days. The viable culture from the highest serial dilution was serially diluted in anaerobic trypticase soy broth culture containing 30 μg/ml of ethidium bromide and maintained at 37° C. under the same conditions for 3 days. This process was repeated another nine times and following the final passage the spirochaetes are washed to remove the ethidium bromide and plated onto Fastidious Anaerobic Agar (LabM) plates to obtain single colonies.

Example 5

Screening for Clones with Cured Plasmids

The single colonies obtained by passage in liquid media containing ethidium bromide were screened by PCR for the loss of plasmid. Three primer pairs targeting ORFs 11-16 are designed for the screening process (FIG. 3). A total of 48 colonies were cell-picked into Tris-EDTA buffer and added as template in PCR reactions using each of the six primer sets. The PCR reactions were performed using HotStarTaq DNA Polymerase (Qiagen) according to the manufacturer's instructions. The absence of PCR product for all primer sets, compared with the presence of all the products in the wild-type *B. hyodysenteriae* WA1 strain, indicated successful plasmid curing.

Example 6

Experimental Infection of Pigs with a Field Strain of *B. Hyodysenteriae* not Containing Virulence Factors (ORFs 11-16)

Thirty-six castrated male pigs (Large White×Landrace× Duroc) of approximately 18 kg body weight were purchased from a commercial piggery that is free of swine dysentery. The pigs were weighed, ear-tagged, and faecal samples were taken and cultured to exclude the possible presence of *Brachyspira hyodysenteriae*. The pigs were randomly assigned to two groups:
i) Group A: twelve pigs that were challenged with virulent *B. hyodysenteriae* strain WA1, ie. a strain that contained the virulence factors identified above in Example 3 (ORFs 11-16); and
ii) Group B: twenty-four pigs that were challenged with a previously uncharacterised field strain of *B. hyodysenteriae* that did not contain the virulence factors identified above in Example 3 (ORFs 11-16), ie. a strain predicted to be avirulent.

Each group was housed in a single pen in a different room of an isolation animal house. Strict biosecurity protocols were maintained to prevent transmission of infection between the rooms. The pigs were fed ad libidum on a weaner diet that did not contain antibiotics.

Two weeks after arrival the pigs in Group A were challenged via stomach tube with 100 ml of a broth containing *B. hyodysenteriae* strain WA1 grown to exponential log-phase ($\sim 10^8$/ml). In the same way, the pigs in Group B were challenged with 100 ml of a broth containing the uncharacterised field strain of *B. hyodysenteriae*, grown to exponential log-phase ($\sim 10^8$/ml). For both groups, the challenge was repeated over three consecutive days.

Following challenge, the pigs were observed daily for clinical signs consistent with swine dysentery, particularly the presence of diarrhoea that contained fresh blood and mucus. Pigs that developed clinical signs of swine dysentery were removed. Bacteriology swabs were taken from rectal faeces of all pigs twice per week, and the swabs were cultured anaerobically on selective agar. The experiment was ended 4 weeks after experimental challenge. Blood was collected from the jugular vein prior to the first day of challenge, and at post-mortem or the end of the experiment. The serum was removed and used for serological analysis in an ELISA.

Example 7

Spirochaetal Culture

Bacteriology swabs were streaked onto Trypticase Soy agar plates containing 5% (v/v) defibrinated sheep blood, 400 ug/ml spectinomycin and 25 ug/ml each of colistin and vancomycin. These plates were incubated at 39° C. in an aerobic environment for seven days. Spirochaetes were identified as B. hyodysenteriae on the basis of strong beta-haemolysis and microscopic morphology. A subset of isolates were subcultured and confirmed as B. hyodysenteriae using a species-specific PCR.

Eleven of the 12 pigs (92%) in Group A shed B. hyodysenteriae in their faeces during the experimental period, and developed signs of swine dysentery. In group B, 13 of the 24 pigs (54%) shed B. hyodysenteriae and developed swine dysentery (see FIG. 5). These difference in shedding pattern and disease between the two groups was statistically significant (P=0.031; Fisher's exact test).

There were no differences in the extent of gross pathology found in the large intestines of the pigs with dysentery in the two groups.

Accordingly, the uncharacterised field strain of B. hyodysenteriae that did not contain the virulence factors identified in Example 3 (ORFs 11-16), colonised significantly fewer pigs, and significantly fewer animals developed disease following challenge, compared to the strain with the virulence factors. This finding indicates that ORFs 11-16 are important in facilitating colonization and allowing the development of disease, supporting the assertion that the ORFs 11-16 encode virulence factors. These results also demonstrate the usefulness of ORFs 11-16 in determining whether a strain of B. hyodysenteriae is virulent or avirulent.

Example 8

Serological ELISA

Microtitre plates were coated with 100 µl per well of sonicated and cleared B. hyodysenteriae whole-cells (1 µg/ml) in carbonate buffer (pH 9.6). The cells were from the same strain used in the respective infections. Coating was allowed to occur at 4° C. overnight. Plates were blocked with 150 µl of PBS-BSA (1% w/v) for 1 hour at room temperature (RT) with mixing and then washed three times with 150 µl of PEST (0.05% v/v). Pig sera were diluted 400-fold in 100 µl of PEST-BSA (0.1% w/v) and incubated at RT for 2 hours with mixing. Plates were washed, (as above) before adding 100 µl of goat anti-swine IgG (whole molecule)-HRP diluted 50,000-fold in PBST-BSA (0.1% w/v). After incubating for 1 hour at RT, the plates were washed and 100 µl of TMB substrate added. Colour development was allowed to occur for 10 minutes at RT before being stopped with the addition of 100.11 of 500 mM sulphuric acid. The optical density of each well was read at 450 nm.

Figure 6:
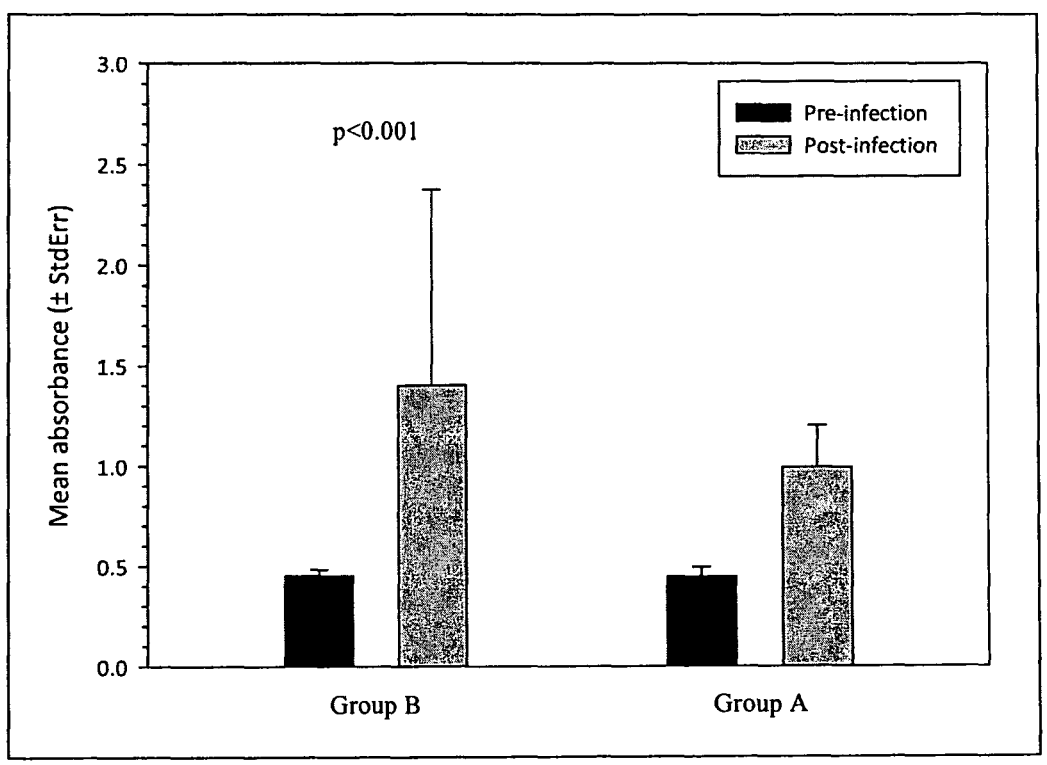
FIG. 6: Levels of antibodies to *B. hyodysenteriae* whole cell preparations measured by ELISA before and after exposure to either virulent *B. hyodysenteriae* strain WA1 (Group A) and an uncharacterised field strain of *B. hyodysenteriae* that did not contain the virulence factors encoded by ORFs 11-16 (Group B).

Pigs from both groups had a similar base-line level of antibodies to B. hyodysenteriae whole cell preparations prior to the experimental challenge. In Group A, 8 of the 12 pigs showed an increase in antibody levels between the time of experimental challenge and the end of the experiment, but over the whole group, the increase in antibody levels was not significant. In Group B, 21 of the 24 pigs showed an increase in antibody levels, and the group increase in antibody levels was significant (p<0.001) (see FIG. 6).

Accordingly, exposure to the field strain of B. hyodysenteriae that did not contain the virulence factors resulted in a systemic immune response evidenced by a is significant increase in antibody levels post B. hyodysenteriae infection. These results indicate that a B. hyodysenteriae strain that does not comprise ORFs 11-16 does have immunogenic properties and could induce protective immunity against a B. hyodysenteriae infection (ie. be protectively immunogenic), even though it has a reduced ability to colonize pigs and cause disease. As such, these results support the assertion that strains of B. hyodysenteriae without functional ORFs would be useful as live vaccine strains.

The invention claimed is:

1. A vaccine composition for vaccinating an animal against *B. hyodysenteriae* infection comprising a non-naturally occurring live strain of *B. hyodysenteriae* and a pharmaceutically acceptable vehicle, wherein:
   (a) said strain has been cured of a plasmid which contained orf 11-16 (SEQ ID NOS:1 to 6); or
   (b) said orf 11-16 (SEQ ID NOS:1 to 6), has been deleted or disrupted in said strain so that no functional product is transcribed or translated from the sequences encoded by said orf 11-16 (SEQ ID NOS:1 to 6); and
   wherein said strain has reduced virulence, with the proviso that the strain is not *Serpulina hyodysenieriae* strain A1 serotype 4 or FM88-90 or derived from said A1 serotype 4 or FM88-90.

2. The vaccine composition of claim 1, wherein the vaccine composition additionally comprises an adjuvant.

3. A method of vaccinating an animal against *B. hyodysenteriae* infection comprising administering to said animal an effective amount of the vaccine composition of claim 1.

4. A kit for vaccination of an animal against *B. hyodvsenteriae* infection comprising:
   (a) the vaccine composition of claim 1; and
   (b) instructions for vaccinating an animal.

5. The vaccine composition of claim 1, wherein the strain retains the immunogenic properties of said *B. hyodysenteriae* strain with said virulence factors encoded by orf 11-16 (SEQ ID NOS:1 to 6) present so as to be protectively immunogenic, but with reduced virulence.

6. A vaccine composition for vaccinating an animal against *B. hyodysenteriae* infection comprising a genetically modified live strain of *B, hyodysenteriae* and a pharmaceutically acceptable vehicle, wherein said strain of *B. hyodysenteriae* has been genetically modified to delete or disrupt virulence factors encoded by orf 11-16 (SEQ ID NOS:1 to 6) and wherein said strain has reduced virulence when compared to the strain before the genetic modification, with the proviso that the strain is not *Serpulina hyodysenteriae* strain A1 serotype 4 or FM88-90 or derived from said A1 serotype 4 or FM88-90.

7. The vaccine composition of claim 6, wherein the vaccine composition additionally comprises an adjuvant.

8. A kit for vaccination of an animal against *B. hyodysenteriae* infection comprising:
   (a) the vaccine composition of claim 6; and
   (b) instructions for vaccinating an animal.

* * * * *

SEQUENCE LISTING

```
<160> NUMBER OF SEQ ID NOS: 90

<210> SEQ ID NO 1
<211> LENGTH: 1218
<212> TYPE: DNA
<213> ORGANISM: Brachyspira hyodysenteriae

<400> SEQUENCE: 1
atggatagta aaaatacaaa atatcagtct aaattaaatc tagaaaatag aacacccttta      60 caagaaataa tacctcttga aacacctttt gtaatgcatt tagattcttc aacagcttgt     120 aatttaaat gtgaattttg tccttctgca tcttctacaa ataaagatta tgtaaaaatg     180
aatttggatt tagatttata taaaaaagct atagatgatt taaaagattt taataataat     240
ttgaaaattc taaggtttta caaaattgga gaacctttaa tgaacagaaa tatagccgaa     300
atggtagcat atgcaagaaa tagcaataaa gtagatttta tagatatgac tacaaatgga     360
tcattattaa ctaatgagtt atcattaaag ttggtagatg ctggattgaa taagatcaac     420
atttcaatag aaggtatcaa ttcagaacaa tataataaat atgctcatta taatataaac     480
```

```
tttaatgaat ttattaataa tttggctttt ttatataaaa ataaaaaaaa cttggaaatt       540
acaatgaaaa taccaggtga ttacttgagt gaaagtgaaa aagaagaatt tttaaatata       600
ttctcaccat attgtgataa aatatttatt gaatatttaa cagataatgt ttggcctaat       660
tttagtgtaa atgaaaattc aaaagtaatt aatttattag gaaaaagtca atatggttta       720
gaagttaaaa atagaaaaat tgttgctat ttattttatg ttttagtatt aaattctaat        780
ggaactataa gtgcttgctg ttcagattgg caagaaaaac ttattatagg tgatgttaga       840
aaacaaagtc ttaagaaat atggaactca gataagatga atgaatttag aattttacat       900
ttaaaaggta aaagatttga aaatgatgtt tgtaaaaatt gcggaaatat acaatcttct       960
caaatagatg atatagatga ttacgctgaa gaaatttat ctagaatgac cagaccagac       1020
cagaccagac cagaccagac cagaccagac cagaccagac cagacctaat atttatatat      1080
gtagcgatta catatatctt tatattaata gaaaatataa aaaaatacaa cctatgttgc      1140
aatataaaat tgcagcatag gttttttat tttagttcta ctattataag gagtgagcaa       1200
ttgtgtcaaa taaagaaa                                                    1218

<210> SEQ ID NO 2
<211> LENGTH: 999
<212> TYPE: DNA
<213> ORGANISM: Brachyspira hyodysenteriae

<400> SEQUENCE: 2
atggcaaaat ttaaatctaa attaaattta gaaactaggc ataaattaga agaagttata        60
ccattaaaaa cacctttttt aatatatttta gatccatcta gtgcttgcaa ctttaaatgt       120
gaattttgtc catctccatt ttctacaaaa gaagattatg taaaacaaat ttttgatttt       180
gaattataca aaaagtaat agatgattta atgaatttg atgataatat caaaatgtta        240
agattccata aaattggaga acctttatta aataagaata tagtcaatat ggttaaatat        300
gctaaagata gtggtaaagt taataatata gatatgacta ctaatggagc tttattgact       360
aaagatatta gcgaaggatt agtaaatgcg ggtatgacac agataaatat atcaatagaa       420
ggaattaatg cagaacaata taaaaaatat gtgcattatg atattgatat aaataattta       480
attgaaaata taaatatttt atacagcata aaagatagtt tggaaataat tataaaaata      540
ccttctaatt atctttcaga agatgataaa aaaatatttt tagatatgtt ttctccttat      600
tgtgatagaa tatttatcga aaacttaagt tccatttggc caaatttcaa tataatggaa      660
aaatcaaata ttataaatat agatgaaaca aaagatcaat ataatatggg attaaaaaat      720
tataaagttt gtacttggcc atttatgct atatgtataa attctaatgg tactgtaagt      780
ccatgtgctt tagattggca ggaaaaatta actgttggag atgtaaaaaa agaaagttta      840
aaaaaaatat ggaattcaga taaattaaac gaacttagaa taagattctt aaaaaagaa      900 gtagaaaata tagatgtatg ttctacttgt ggtaatttaa aatattgtca agtagataat      960
atagatgatt atgctgaaga aatttaaaaa aggattta                              999

<210> SEQ ID NO 3
<211> LENGTH: 1008
<212> TYPE: DNA
<213> ORGANISM: Brachyspira hyodysenteriae

<400> SEQUENCE: 3
atgaaagcta aaataaaacc tagaatagat ttagaaaaca gaactaaatt agaaacggta        60
atcccattag aaacaccttt tattatattt atagatccat ctgataaatg taattcaaa       120
```

```
tgtaagttttt gtccaacagg aaatattgaa cttatgcaaa atacatctgg cagaaatttt      180
ggttctatgg attttaattt atataaaaaa attatagatg atttacagca atttgaagga      240
aaggttaagg ttataagact ttataaagat ggagaaccac tacttaataa gcattttgct      300
gaaatggtag agtatgcaaa aaaatctgat aaagtaaata gggtagatac tactactaat      360
gcttcgcttt taaacaaaga tttatcatta caaattataa atgctggact ggatagaata      420
aatatttcta tagaaggtat gaattctcaa caatatcttg attttcaaa agctaatgtt       480 aactttgaaa aactagtgga aaatataact tttttctatg agaataggaa acaatgtgaa      540
atgattgtaa aaattaatgg agacataata tctgaagaac aaaagcagga attttataat      600
atatttggtg aaattgctga tggagtaaat atagaaagtg taatgtcttg ctggcctgaa      660
tttgaacttg atggaataag tgtaaacatg gaaagaggta tttatggaca agaaataaag      720
gaagtaatgg tttgtcctta tgtatttat tctatgtcaa taaactctac aggtattgcc       780
agtgcttgtt atttagactg ggaaagaaag cttattatag gtgatgtcaa taagaatca        840 gtaaaaacta tatggaatag caatgaaatg aataatttaa gaaaattatt cttaaaaaaa      900
gaacgtaaat cccatcctat atgcaaaaat tgcggacagc ttactcatgg tatgcctgat      960
aatattgatg attatgctga tgaattatta aataaaataa gtatatta                  1008

<210> SEQ ID NO 4
<211> LENGTH: 1263
<212> TYPE: DNA
<213> ORGANISM: Brachyspira hyodysenteriae

<400> SEQUENCE: 4
atgaataaaa taaaaatatt gcatattact ccgcatcttg gtggaggagt tggtacagta       60
ttattagatt ggtttaaata cgaaaaaaat gataaatatt ttcaacattc tgttatatgt      120
ttggattatg ctaatgaaaa atcaaaaaaa atactaaaag aattagaact tcaattaaaa      180
gataatatgt atcaaaatga gcatgaaatt ttaaatgata taaaaaaatc agatattgta      240
ttaatgcatt tttggaatca tcctcttctt tatcatttca ttattaaaaa tgaattaccct     300 gaatgcagat taattttgtg gtcacatatt tcaggtataa atccgcctaa tgtatttaca      360
aataaaatat taaattatcc tgataaattc atatttacaa ctccaatgag ctttaaaact      420
aaagaaatta tagaatatag caataaaaat tcaattatat caatatggtc aacatcaat      480 ttaactaaat atttaaattt aaaaaaagaa ataatcact tttaatgt tttatatata       540 ggtactgttg ataatgctaa aatgtataat aattttgtag aattatgtaa taagattaat      600
atagataata ttaagtttat agttgtaggc ggtcctaatc atttgaaatt agaagaatat      660
actaagaaat tagggatatc taataagttt attttactg gtaaagtaga agatataatt     720
ccatatttaa aaattagtaa tgtatttgga tatcctttaa caagtggtca ttttggtacc      780
tgtgaccaat ctatacaaga agctatgact gctggtttag tacctgttgt ttttgacaat      840
gaaatggaaa atctatgat taataatgac tgcggtttta tatgtaagaa tgaagatgaa       900
tatgttcagt ctatagaaaa attacgtaac gataaaaatt tattaaaacg aatgcaagaa      960
aattcaaaaa actatgctat aaaagagttt tctatagaaa gaatgtcaaa agattggaat     1020
aaagtattta tgaaattat gattatacaa aaacttata aaaatggaa tatagataat        1080 actaatataa aaactataga tatattttt gaaagtttag gtgaatacaa aaaaatattt      1140
gatcttcctt ttgaaaagtt aaagaaagaa ttgtcaaaac caaactggac ttcaaattct     1200
```

```
aagggtaccc atctgcaata taaatctttt cttgatgatg aagtttgga caaatttata    1260 ttt                                                                 1263

<210> SEQ ID NO 5
<211> LENGTH: 858
<212> TYPE: DNA
<213> ORGANISM: Brachyspira hyodysenteriae

<400> SEQUENCE: 5
atgaaaaaag taatagtaac tggaataaat ggacttatag gtcaatatat atctaaacct     60
ttagaagaat taggttttga agttttttggc ataggaacta atccataaa aaaaagtaat    120 tattgttcta tggatttaaa tgatcatata aaattagaaa atattttaa agaaataaaa     180 cctgaatatt taatacattt agcttgggac actaaaaaag ctatttaga atctgaagct     240 aattttgatt tattatattc atctataaaa atgcttaaat attttaaaga aatggcgga     300 aaaaaaactg tatttgtagg tacttgtttt gaatataaat ttaaagatac accattaaaa    360
gaaaatgatg accttaatcc tacaacaata tatgctaaaa ctaaaaatta tttaagggaa    420
atgtctgaat tatactctat taaaaataat atagattttt gttggggtag agttttctat    480
acttatggag ataatgaaaa tccaaataga cttttcccgc atattattaa ttctctaaaa    540
gaagataaaa aagtttctat aaattattca caattaaaaa aagattatat atttgctggt    600
gatatagcaa aaagtatagc tttaattatt gattcaaatg ttaatggtat tatcaattta    660
tgtacatcaa atacaattag tttggaagaa atagctttaa ccattgctaa aaaatttaat    720
aaaattaact tattagaatt aaaaaaatta aacactgaag aacctaaaat tattgtaggg    780
gataattccc gcttagttaa tgaataggc tttaaaaatt ttactacagt aggtgaatgg    840
gtaaacaaat atttaaat                                                  858

<210> SEQ ID NO 6
<211> LENGTH: 564
<212> TYPE: DNA
<213> ORGANISM: Brachyspira hyodysenteriae

<400> SEQUENCE: 6
gtgggaaaaa taaatctgaa ggaaattaat attatgacta tagaaaaaac aaatatagaa     60
ggtgcatata taatacaaaa taattatata gaagatgaaa gaggtatatt cttaagactt    120
ttttgtaatg atgaacttaa aaaatcaggt attgattttg aagtaaaaca gtcaaatatg    180
agttatagtg ctaaaaaagg aacattaaga gggatgcatt atcagattgc tccttatgca    240
gaaataaaag ttgtaagatg tataaaggga aaagttttttg atgcaatagc tgatataaga    300
aaagattcgc ctactttttgg tcagcatttt actgtagaat taagcgaaga gaatggaaaa    360
atgatttata tacctcctta tgtggctcat ggaatagaaa ctcttgaaga tcatagtatg    420
atatgttatt ttgttggagc ttcttttgta ccaaatgctt atggatatt gagatggaat    480 gatcctttt ttaatattga ttggcctata aaagataatc taattatgag tgaaaaggat    540
aaaagtatac cagattttga atat                                          564

<210> SEQ ID NO 7
<211> LENGTH: 406
<212> TYPE: PRT
<213> ORGANISM: Brachyspira hyodysenteriae

<400> SEQUENCE: 7

Met Asp Ser Lys Asn Thr Lys Tyr Gln Ser Lys Leu Asn Leu Glu Asn
```

```
  1               5                  10                  15
Arg Thr Pro Leu Gln Glu Ile Ile Pro Leu Glu Thr Pro Phe Val Met
            20                  25                  30

His Leu Asp Ser Ser Thr Ala Cys Asn Phe Lys Cys Glu Phe Cys Pro
            35                  40                  45

Ser Ala Ser Ser Thr Asn Lys Asp Tyr Val Lys Met Asn Leu Asp Leu
 50              55                  60

Asp Leu Tyr Lys Lys Ala Ile Asp Asp Leu Lys Asp Phe Asn Asn Asn
 65                  70                  75                  80

Leu Lys Ile Leu Arg Phe Tyr Lys Ile Gly Glu Pro Leu Met Asn Arg
                 85                  90                  95

Asn Ile Ala Glu Met Val Ala Tyr Ala Arg Asn Ser Asn Lys Val Asp
                100                 105                 110

Phe Ile Asp Met Thr Thr Asn Gly Ser Leu Leu Thr Asn Glu Leu Ser
                115                 120                 125

Leu Lys Leu Val Asp Ala Gly Leu Asn Lys Ile Asn Ile Ser Ile Glu
            130                 135                 140

Gly Ile Asn Ser Glu Gln Tyr Asn Lys Tyr Ala His Tyr Asn Ile Asn
145                 150                 155                 160

Phe Asn Glu Phe Ile Asn Asn Leu Ala Phe Leu Tyr Lys Asn Lys Lys
                165                 170                 175

Asn Leu Glu Ile Thr Met Lys Ile Pro Gly Asp Tyr Leu Ser Glu Ser
                180                 185                 190

Glu Lys Glu Glu Phe Leu Asn Ile Phe Ser Pro Tyr Cys Asp Lys Ile
            195                 200                 205

Phe Ile Glu Tyr Leu Thr Asp Asn Val Trp Pro Asn Phe Ser Val Asn
210                 215                 220

Glu Asn Ser Lys Val Ile Asn Leu Leu Gly Lys Ser Gln Tyr Gly Leu
225                 230                 235                 240

Glu Val Lys Asn Arg Lys Ile Cys Cys Tyr Leu Phe Tyr Val Leu Val
                245                 250                 255

Leu Asn Ser Asn Gly Thr Ile Ser Ala Cys Cys Ser Asp Trp Gln Glu
                260                 265                 270

Lys Leu Ile Ile Gly Asp Val Arg Lys Gln Ser Leu Lys Glu Ile Trp
            275                 280                 285

Asn Ser Asp Lys Met Asn Glu Phe Arg Ile Leu His Leu Lys Gly Lys
            290                 295                 300

Arg Phe Glu Asn Asp Val Cys Lys Asn Cys Gly Asn Ile Gln Ser Ser
305                 310                 315                 320

Gln Ile Asp Asp Ile Asp Asp Tyr Ala Glu Glu Ile Leu Ser Arg Met
                325                 330                 335

Thr Arg Pro Asp Gln Thr Arg Pro Asp Gln Thr Arg Pro Asp Gln Thr
                340                 345                 350

Arg Pro Asp Leu Ile Phe Ile Tyr Val Ala Ile Thr Tyr Ile Phe Ile
                355                 360                 365

Leu Ile Glu Asn Ile Lys Lys Tyr Asn Leu Cys Cys Asn Ile Lys Leu
            370                 375                 380

Gln His Arg Phe Phe Tyr Phe Ser Ser Thr Ile Arg Ser Glu Gln
385                 390                 395                 400

Leu Cys Gln Ile Lys Lys
            405
```

<210> SEQ ID NO 8

```
<211> LENGTH: 333
<212> TYPE: PRT
<213> ORGANISM: Brachyspira hyodysenteriae

<400> SEQUENCE: 8
```

| | | | | | | | | | | | | | | |
|---|---|---|---|---|---|---|---|---|---|---|---|---|---|---|
|Met|Ala|Lys|Phe|Lys|Ser|Lys|Leu|Asn|Leu|Glu|Thr|Arg|His|Lys|Leu|
|1| | | |5| | | | |10| | | | |15| |

| | | | | | | | | | | | | | | |
|---|---|---|---|---|---|---|---|---|---|---|---|---|---|---|
|Glu|Glu|Val|Ile|Pro|Leu|Lys|Thr|Pro|Phe|Leu|Ile|Tyr|Leu|Asp|Pro|
| | | |20| | | | |25| | | | |30| | |

| | | | | | | | | | | | | | | |
|---|---|---|---|---|---|---|---|---|---|---|---|---|---|---|
|Ser|Ser|Ala|Cys|Asn|Phe|Lys|Cys|Glu|Phe|Cys|Pro|Ser|Pro|Phe|Ser|
| | | |35| | | | |40| | | | |45| | |

Thr Lys Glu Asp Tyr Val Lys Gln Ile Phe Asp Phe Glu Leu Tyr Lys
            50                  55                  60

Lys Val Ile Asp Asp Leu Asn Glu Phe Asp Asp Asn Ile Lys Met Leu
65                  70                  75                  80

Arg Phe His Lys Ile Gly Glu Pro Leu Leu Asn Lys Asn Ile Val Asn
                85                  90                  95

Met Val Lys Tyr Ala Lys Asp Ser Gly Lys Val Asn Asn Ile Asp Met
            100                 105                 110

Thr Thr Asn Gly Ala Leu Leu Thr Lys Asp Ile Ser Glu Gly Leu Val
        115                 120                 125

Asn Ala Gly Met Thr Gln Ile Asn Ile Ser Ile Glu Gly Ile Asn Ala
130                 135                 140

Glu Gln Tyr Lys Lys Tyr Val His Tyr Asp Ile Asp Ile Asn Asn Leu
145                 150                 155                 160

Ile Glu Asn Ile Lys Tyr Leu Tyr Ser Ile Lys Asp Ser Leu Glu Ile
                165                 170                 175

Ile Ile Lys Ile Pro Ser Asn Tyr Leu Ser Glu Asp Lys Lys Ile
            180                 185                 190

Phe Leu Asp Met Phe Ser Pro Tyr Cys Asp Arg Ile Phe Ile Glu Asn
        195                 200                 205

Leu Ser Ser Ile Trp Pro Asn Phe Asn Ile Met Glu Lys Ser Asn Ile
    210                 215                 220

Ile Asn Ile Asp Glu Thr Lys Asp Gln Tyr Asn Met Gly Leu Lys Asn
225                 230                 235                 240

Tyr Lys Val Cys Thr Trp Pro Phe Tyr Ala Ile Cys Ile Asn Ser Asn
                245                 250                 255

Gly Thr Val Ser Pro Cys Ala Leu Asp Trp Gln Glu Lys Leu Thr Val
            260                 265                 270

Gly Asp Val Lys Lys Glu Ser Leu Lys Lys Ile Trp Asn Ser Asp Lys
        275                 280                 285

Leu Asn Glu Leu Arg Ile Arg Phe Leu Lys Lys Glu Val Glu Asn Ile
    290                 295                 300

Asp Val Cys Ser Thr Cys Gly Asn Leu Lys Tyr Cys Gln Val Asp Asn
305                 310                 315                 320

Ile Asp Asp Tyr Ala Glu Glu Ile Leu Lys Arg Ile Leu
                325                 330

```
<210> SEQ ID NO 9
<211> LENGTH: 336
<212> TYPE: PRT
<213> ORGANISM: Brachyspira hyodysenteriae

<400> SEQUENCE: 9
```

Met Lys Ala Lys Ile Lys Pro Arg Ile Asp Leu Glu Asn Arg Thr Lys
1               5                   10                  15

```
Leu Glu Thr Val Ile Pro Leu Glu Thr Pro Phe Ile Phe Ile Asp
            20                  25                  30

Pro Ser Asp Lys Cys Asn Phe Lys Cys Lys Phe Cys Pro Thr Gly Asn
        35                  40                  45

Ile Glu Leu Met Gln Asn Thr Ser Gly Arg Asn Phe Gly Ser Met Asp
 50                  55                  60

Phe Asn Leu Tyr Lys Lys Ile Asp Asp Leu Gln Gln Phe Glu Gly
 65                  70                  75                  80

Lys Val Lys Val Ile Arg Leu Tyr Lys Asp Gly Pro Leu Leu Asn
                85                  90                  95

Lys His Phe Ala Glu Met Val Glu Tyr Ala Lys Ser Asp Lys Val
                100                 105                 110

Asn Arg Val Asp Thr Thr Thr Asn Ala Ser Leu Leu Asn Lys Asp Leu
            115                 120                 125

Ser Leu Gln Ile Ile Asn Ala Gly Leu Asp Arg Ile Asn Ile Ser Ile
130                 135                 140

Glu Gly Met Asn Ser Gln Gln Tyr Leu Asp Phe Ser Lys Ala Asn Val
145                 150                 155                 160

Asn Phe Glu Lys Leu Val Glu Asn Ile Thr Phe Phe Tyr Glu Asn Arg
                165                 170                 175

Lys Gln Cys Glu Met Ile Val Lys Ile Asn Gly Asp Ile Ile Ser Glu
            180                 185                 190

Glu Gln Lys Gln Glu Phe Tyr Asn Ile Phe Gly Glu Ile Ala Asp Gly
            195                 200                 205

Val Asn Ile Glu Ser Val Met Ser Cys Trp Pro Glu Phe Glu Leu Asp
210                 215                 220

Gly Ile Ser Val Asn Met Glu Arg Gly Ile Tyr Gly Gln Glu Ile Lys
225                 230                 235                 240

Glu Val Met Val Cys Pro Tyr Val Phe Tyr Ser Met Ser Ile Asn Ser
                245                 250                 255

Thr Gly Ile Ala Ser Ala Cys Tyr Leu Asp Trp Glu Arg Lys Leu Ile
            260                 265                 270

Ile Gly Asp Val Asn Lys Glu Ser Val Lys Thr Ile Trp Asn Ser Asn
            275                 280                 285

Glu Met Asn Asn Leu Arg Lys Leu Phe Leu Lys Lys Glu Arg Lys Ser
290                 295                 300

His Pro Ile Cys Lys Asn Cys Gly Gln Leu Thr His Gly Met Pro Asp
305                 310                 315                 320

Asn Ile Asp Asp Tyr Ala Asp Glu Leu Leu Asn Lys Ile Ser Ile Leu
                325                 330                 335

<210> SEQ ID NO 10
<211> LENGTH: 421
<212> TYPE: PRT
<213> ORGANISM: Brachyspira hyodysenteriae

<400> SEQUENCE: 10

Met Asn Lys Ile Lys Ile Leu His Ile Thr Pro His Leu Gly Gly Gly
1               5                   10                  15

Val Gly Thr Val Leu Leu Asp Trp Phe Lys Tyr Glu Lys Asn Asp Lys
                20                  25                  30

Tyr Phe Gln His Ser Val Ile Cys Leu Asp Tyr Ala Asn Glu Lys Ser
            35                  40                  45

Lys Lys Ile Leu Lys Glu Leu Glu Leu Gln Leu Lys Asp Asn Met Tyr
```

```
                50                  55                  60
Gln Asn Glu His Glu Ile Leu Asn Asp Ile Lys Lys Ser Asp Ile Val
 65                  70                  75                  80

Leu Met His Phe Trp Asn His Pro Leu Leu Tyr His Phe Ile Ile Lys
                     85                  90                  95

Asn Glu Leu Pro Glu Cys Arg Leu Ile Leu Trp Ser His Ile Ser Gly
                100                 105                 110

Ile Asn Pro Pro Asn Val Phe Thr Asn Lys Ile Leu Asn Tyr Pro Asp
                115                 120                 125

Lys Phe Ile Phe Thr Thr Pro Met Ser Phe Lys Thr Lys Glu Ile Ile
            130                 135                 140

Glu Tyr Ser Asn Lys Asn Ser Ile Ile Ser Ile Trp Ser Thr Ser Asn
145                 150                 155                 160

Leu Thr Lys Tyr Leu Asn Leu Lys Lys Glu Asn Asn His Phe Phe Asn
                165                 170                 175

Val Leu Tyr Ile Gly Thr Val Asp Asn Ala Lys Met Tyr Asn Asn Phe
                180                 185                 190

Val Glu Leu Cys Asn Lys Ile Asn Ile Asp Asn Ile Lys Phe Ile Val
            195                 200                 205

Val Gly Gly Pro Asn His Leu Lys Leu Glu Glu Tyr Thr Lys Lys Leu
210                 215                 220

Gly Ile Ser Asn Lys Phe Ile Phe Thr Gly Lys Val Glu Asp Ile Ile
225                 230                 235                 240

Pro Tyr Leu Lys Ile Ser Asn Val Phe Gly Tyr Pro Leu Thr Ser Gly
                245                 250                 255

His Phe Gly Thr Cys Asp Gln Ser Ile Gln Glu Ala Met Thr Ala Gly
                260                 265                 270

Leu Val Pro Val Val Phe Asp Asn Glu Met Glu Lys Ser Met Ile Asn
            275                 280                 285

Asn Asp Cys Gly Phe Ile Cys Lys Asn Glu Asp Glu Tyr Val Gln Ser
290                 295                 300

Ile Glu Lys Leu Arg Asn Asp Lys Asn Leu Leu Lys Arg Met Gln Glu
305                 310                 315                 320

Asn Ser Lys Asn Tyr Ala Ile Lys Glu Phe Ser Ile Glu Arg Met Ser
                325                 330                 335

Lys Asp Trp Asn Lys Val Phe Asn Glu Ile Met Ile Gln Lys Thr
                340                 345                 350

Tyr Lys Lys Trp Asn Ile Asp Asn Thr Asn Ile Lys Thr Ile Asp Ile
            355                 360                 365

Phe Phe Glu Ser Leu Gly Glu Tyr Lys Lys Ile Phe Asp Leu Pro Phe
            370                 375                 380

Glu Lys Leu Lys Lys Glu Leu Ser Lys Pro Asn Trp Thr Ser Asn Ser
385                 390                 395                 400

Lys Gly Thr His Leu Gln Tyr Lys Ser Phe Leu Asp Asp Gly Ser Leu
                405                 410                 415

Asp Lys Phe Ile Phe
            420

<210> SEQ ID NO 11
<211> LENGTH: 286
<212> TYPE: PRT
<213> ORGANISM: Brachyspira hyodysenteriae

<400> SEQUENCE: 11
```

```
Met Lys Lys Val Ile Val Thr Gly Ile Asn Gly Leu Ile Gly Gln Tyr
1               5                   10                  15

Ile Ser Lys Pro Leu Glu Glu Leu Gly Phe Glu Val Phe Gly Ile Gly
            20                  25                  30

Thr Lys Ser Ile Lys Lys Ser Asn Tyr Cys Ser Met Asp Leu Asn Asp
            35                  40                  45

His Ile Lys Leu Glu Asn Ile Phe Lys Glu Ile Lys Pro Glu Tyr Leu
50                  55                  60

Ile His Leu Ala Trp Asp Thr Lys Gly Tyr Leu Glu Ser Glu Ala
65                  70                  75                  80

Asn Phe Asp Leu Leu Tyr Ser Ser Ile Lys Met Leu Lys Tyr Phe Lys
                85                  90                  95

Glu Asn Gly Gly Lys Lys Thr Val Phe Val Gly Thr Cys Phe Glu Tyr
                100                 105                 110

Lys Phe Lys Asp Thr Pro Leu Lys Glu Asn Asp Leu Asn Pro Thr
            115                 120                 125

Thr Ile Tyr Ala Lys Thr Lys Asn Tyr Leu Arg Glu Met Ser Glu Leu
            130                 135                 140

Tyr Ser Ile Lys Asn Asn Ile Asp Phe Cys Trp Gly Arg Val Phe Tyr
145                 150                 155                 160

Thr Tyr Gly Asp Asn Glu Asn Pro Asn Arg Leu Phe Pro His Ile Ile
                165                 170                 175

Asn Ser Leu Lys Glu Asp Lys Lys Val Ser Ile Asn Tyr Ser Gln Leu
                180                 185                 190

Lys Lys Asp Tyr Ile Phe Ala Gly Asp Ile Ala Lys Ser Ile Ala Leu
            195                 200                 205

Ile Ile Asp Ser Asn Val Asn Gly Ile Ile Asn Leu Cys Thr Ser Asn
210                 215                 220

Thr Ile Ser Leu Glu Glu Ile Ala Leu Thr Ile Ala Lys Lys Phe Asn
225                 230                 235                 240

Lys Ile Asn Leu Leu Glu Leu Lys Lys Leu Asn Thr Glu Glu Pro Lys
                245                 250                 255

Ile Ile Val Gly Asp Asn Ser Arg Leu Val Asn Glu Ile Gly Phe Lys
            260                 265                 270

Asn Phe Thr Thr Val Gly Glu Trp Val Asn Lys Tyr Leu Asn
            275                 280                 285

<210> SEQ ID NO 12
<211> LENGTH: 188
<212> TYPE: PRT
<213> ORGANISM: Brachyspira hyodysenteriae

<400> SEQUENCE: 12

Val Gly Lys Ile Asn Leu Lys Glu Ile Asn Ile Met Thr Ile Glu Lys
1               5                   10                  15

Thr Asn Ile Glu Gly Ala Tyr Ile Ile Gln Asn Asn Tyr Ile Glu Asp
            20                  25                  30

Glu Arg Gly Tyr Phe Leu Arg Leu Phe Cys Asn Asp Glu Leu Lys Lys
            35                  40                  45

Ser Gly Ile Asp Phe Glu Val Lys Gln Ser Asn Met Ser Tyr Ser Ala
        50                  55                  60

Lys Lys Gly Thr Leu Arg Gly Met His Tyr Gln Ile Ala Pro Tyr Ala
65                  70                  75                  80

Glu Ile Lys Val Val Arg Cys Ile Lys Gly Lys Val Phe Asp Ala Ile
                85                  90                  95
```

```
Ala Asp Ile Arg Lys Asp Ser Pro Thr Phe Gly Gln His Phe Thr Val
            100                 105                 110

Glu Leu Ser Glu Glu Asn Gly Lys Met Ile Tyr Ile Pro Pro Tyr Val
        115                 120                 125

Ala His Gly Ile Glu Thr Leu Glu Asp His Ser Met Ile Cys Tyr Phe
130                 135                 140

Val Gly Ala Ser Phe Val Pro Asn Ala Tyr Gly Tyr Leu Arg Trp Asn
145                 150                 155                 160

Asp Pro Phe Phe Asn Ile Asp Trp Pro Ile Lys Asp Asn Leu Ile Met
                165                 170                 175

Ser Glu Lys Asp Lys Ser Ile Pro Asp Phe Glu Tyr
            180                 185

<210> SEQ ID NO 13
<211> LENGTH: 26
<212> TYPE: DNA
<213> ORGANISM: Artificial sequence
<220> FEATURE:
<223> OTHER INFORMATION: Synthetic

<400> SEQUENCE: 13
actggagttg ctggatttat aggatc                                        26

<210> SEQ ID NO 14
<211> LENGTH: 23
<212> TYPE: DNA
<213> ORGANISM: Artificial sequence
<220> FEATURE:
<223> OTHER INFORMATION: Synthetic

<400> SEQUENCE: 14
aagtcaggtc tctgtctctt tcc                                           23

<210> SEQ ID NO 15
<211> LENGTH: 30
<212> TYPE: DNA
<213> ORGANISM: Artificial sequence
<220> FEATURE:
<223> OTHER INFORMATION: Synthetic

<400> SEQUENCE: 15
caaataaaga tcatactgtt ataggaatag                                    30

<210> SEQ ID NO 16
<211> LENGTH: 21
<212> TYPE: DNA
<213> ORGANISM: Artificial sequence
<220> FEATURE:
<223> OTHER INFORMATION: Synthetic

<400> SEQUENCE: 16
atgtatagtc acgcatagtg g                                             21

<210> SEQ ID NO 17
<211> LENGTH: 24
<212> TYPE: DNA
<213> ORGANISM: Artificial sequence
<220> FEATURE:
<223> OTHER INFORMATION: Synthetic

<400> SEQUENCE: 17
tgtaatacat ttagcaggat atgg                                          24
```

<210> SEQ ID NO 18
<211> LENGTH: 26
<212> TYPE: DNA
<213> ORGANISM: Artificial sequence
<220> FEATURE:
<223> OTHER INFORMATION: Synthetic

<400> SEQUENCE: 18
ggtataggat tattttcaag tatcag                                         26

<210> SEQ ID NO 19
<211> LENGTH: 26
<212> TYPE: DNA
<213> ORGANISM: Artificial sequence
<220> FEATURE:
<223> OTHER INFORMATION: Synthetic

<400> SEQUENCE: 19
gttcatacca tttagaaaaa gaagag                                         26

<210> SEQ ID NO 20
<211> LENGTH: 26
<212> TYPE: DNA
<213> ORGANISM: Artificial sequence
<220> FEATURE:
<223> OTHER INFORMATION: Synthetic

<400> SEQUENCE: 20
gttcatacca tttagaaaaa gaagag                                         26

<210> SEQ ID NO 21
<211> LENGTH: 23
<212> TYPE: DNA
<213> ORGANISM: Artificial sequence
<220> FEATURE:
<223> OTHER INFORMATION: Synthetic

<400> SEQUENCE: 21
agaacaaaac aacataaagc atc                                            23

<210> SEQ ID NO 22
<211> LENGTH: 24
<212> TYPE: DNA
<213> ORGANISM: Artificial sequence
<220> FEATURE:
<223> OTHER INFORMATION: Synthetic

<400> SEQUENCE: 22
catcagtaaa acaaatataa tccc                                           24

<210> SEQ ID NO 23
<211> LENGTH: 20
<212> TYPE: DNA
<213> ORGANISM: Artificial sequence
<220> FEATURE:
<223> OTHER INFORMATION: Synthetic

<400> SEQUENCE: 23
cctgagcatt atggactttc                                                20

<210> SEQ ID NO 24
<211> LENGTH: 24
<212> TYPE: DNA
<213> ORGANISM: Artificial sequence
<220> FEATURE:
<223> OTHER INFORMATION: Synthetic

<400> SEQUENCE: 24
tgtactgtct gatttttat ggtc                                          24

<210> SEQ ID NO 25
<211> LENGTH: 24
<212> TYPE: DNA
<213> ORGANISM: Artificial sequence
<220> FEATURE:
<223> OTHER INFORMATION: Synthetic

<400> SEQUENCE: 25
aaatgtagaa gatattgtat tgcc                                         24

<210> SEQ ID NO 26
<211> LENGTH: 28
<212> TYPE: DNA
<213> ORGANISM: Artificial sequence
<220> FEATURE:
<223> OTHER INFORMATION: Synthetic

<400> SEQUENCE: 26
acctctccta tatgtttttt atacttag                                     28

<210> SEQ ID NO 27
<211> LENGTH: 30
<212> TYPE: DNA
<213> ORGANISM: Artificial sequence
<220> FEATURE:
<223> OTHER INFORMATION: Synthetic

<400> SEQUENCE: 27
attactacaa aatgtactct aaaatgtaag                                   30

<210> SEQ ID NO 28
<211> LENGTH: 29
<212> TYPE: DNA
<213> ORGANISM: Artificial sequence
<220> FEATURE:
<223> OTHER INFORMATION: Synthetic

<400> SEQUENCE: 28
ccatactata tgacaaaaat aaaatctag                                    29

<210> SEQ ID NO 29
<211> LENGTH: 30
<212> TYPE: DNA
<213> ORGANISM: Artificial sequence
<220> FEATURE:
<223> OTHER INFORMATION: Synthetic

<400> SEQUENCE: 29
tatctaagta taaaaaacat ataggagagg                                   30

<210> SEQ ID NO 30
<211> LENGTH: 21
<212> TYPE: DNA
<213> ORGANISM: Artificial sequence
<220> FEATURE:
<223> OTHER INFORMATION: Synthetic

<400> SEQUENCE: 30
cagcacaaaa ctcacatagt g                                            21

<210> SEQ ID NO 31

```
<211> LENGTH: 25
<212> TYPE: DNA
<213> ORGANISM: Artificial sequence
<220> FEATURE:
<223> OTHER INFORMATION: Synthetic

<400> SEQUENCE: 31
aaatacttgt caataatctt agtgg                                         25

<210> SEQ ID NO 32
<211> LENGTH: 25
<212> TYPE: DNA
<213> ORGANISM: Artificial sequence
<220> FEATURE:
<223> OTHER INFORMATION: Synthetic

<400> SEQUENCE: 32
tttcatcata agcaaaaata atatc                                         25

<210> SEQ ID NO 33
<211> LENGTH: 26
<212> TYPE: DNA
<213> ORGANISM: Artificial sequence
<220> FEATURE:
<223> OTHER INFORMATION: Synthetic

<400> SEQUENCE: 33
gtaagtggaa aaagaatgaa acatac                                        26

<210> SEQ ID NO 34
<211> LENGTH: 22
<212> TYPE: DNA
<213> ORGANISM: Artificial sequence
<220> FEATURE:
<223> OTHER INFORMATION: Synthetic

<400> SEQUENCE: 34
agattgtctt gacgaataaa ag                                            22

<210> SEQ ID NO 35
<211> LENGTH: 30
<212> TYPE: DNA
<213> ORGANISM: Artificial sequence
<220> FEATURE:
<223> OTHER INFORMATION: Synthetic

<400> SEQUENCE: 35
aataaatatg acattaaagg aataaaaatc                                    30

<210> SEQ ID NO 36
<211> LENGTH: 30
<212> TYPE: DNA
<213> ORGANISM: Artificial sequence
<220> FEATURE:
<223> OTHER INFORMATION: Synthetic

<400> SEQUENCE: 36
ctattgttag tagcaaaata ataaaaatac                                    30

<210> SEQ ID NO 37
<211> LENGTH: 30
<212> TYPE: DNA
<213> ORGANISM: Artificial sequence
<220> FEATURE:
<223> OTHER INFORMATION: Synthetic

<400> SEQUENCE: 37
```

-continued

```
taaatgaagt atataataaa aatgaaaaag                                      30

<210> SEQ ID NO 38
<211> LENGTH: 22
<212> TYPE: DNA
<213> ORGANISM: Artificial sequence
<220> FEATURE:
<223> OTHER INFORMATION: Synthetic

<400> SEQUENCE: 38
aataaacatg aagaatggtg tc                                              22

<210> SEQ ID NO 39
<211> LENGTH: 28
<212> TYPE: DNA
<213> ORGANISM: Artificial sequence
<220> FEATURE:
<223> OTHER INFORMATION: Synthetic

<400> SEQUENCE: 39
ataaaccaaa tgatttatta actatacc                                        28

<210> SEQ ID NO 40
<211> LENGTH: 28
<212> TYPE: DNA
<213> ORGANISM: Artificial sequence
<220> FEATURE:
<223> OTHER INFORMATION: Synthetic

<400> SEQUENCE: 40
ggtgtcttaa tgctaattta tattctag                                        28

<210> SEQ ID NO 41
<211> LENGTH: 23
<212> TYPE: DNA
<213> ORGANISM: Artificial sequence
<220> FEATURE:
<223> OTHER INFORMATION: Synthetic

<400> SEQUENCE: 41
aaattagcat taagacacca ttc                                             23

<210> SEQ ID NO 42
<211> LENGTH: 27
<212> TYPE: DNA
<213> ORGANISM: Artificial sequence
<220> FEATURE:
<223> OTHER INFORMATION: Synthetic

<400> SEQUENCE: 42
caagtttatt tagttttctt ttctgac                                         27

<210> SEQ ID NO 43
<211> LENGTH: 27
<212> TYPE: DNA
<213> ORGANISM: Artificial sequence
<220> FEATURE:
<223> OTHER INFORMATION: Synthetic

<400> SEQUENCE: 43
atttagaaga tgtaatacct ttagagg                                         27

<210> SEQ ID NO 44
<211> LENGTH: 25
<212> TYPE: DNA
```

<210> SEQ ID NO 44
<211> LENGTH: 25
<212> TYPE: DNA
<213> ORGANISM: Artificial sequence
<220> FEATURE:
<223> OTHER INFORMATION: Synthetic

<400> SEQUENCE: 44
tcattttcgc tatattttta tttac                                          25

<210> SEQ ID NO 45
<211> LENGTH: 25
<212> TYPE: DNA
<213> ORGANISM: Artificial sequence
<220> FEATURE:
<223> OTHER INFORMATION: Synthetic

<400> SEQUENCE: 45
ttatacaaaa taggagagcc tttag                                          25

<210> SEQ ID NO 46
<211> LENGTH: 20
<212> TYPE: DNA
<213> ORGANISM: Artificial sequence
<220> FEATURE:
<223> OTHER INFORMATION: Synthetic

<400> SEQUENCE: 46
atcgcaataa tctgaaaatg                                                20

<210> SEQ ID NO 47
<211> LENGTH: 30
<212> TYPE: DNA
<213> ORGANISM: Artificial sequence
<220> FEATURE:
<223> OTHER INFORMATION: Synthetic

<400> SEQUENCE: 47
gtatgtactt atctttttta ttctattgtc                                     30

<210> SEQ ID NO 48
<211> LENGTH: 25
<212> TYPE: DNA
<213> ORGANISM: Artificial sequence
<220> FEATURE:
<223> OTHER INFORMATION: Synthetic

<400> SEQUENCE: 48
catattggat ttttatctct atgtc                                          25

<210> SEQ ID NO 49
<211> LENGTH: 22
<212> TYPE: DNA
<213> ORGANISM: Artificial sequence
<220> FEATURE:
<223> OTHER INFORMATION: Synthetic

<400> SEQUENCE: 49
attggataga acatagaggg ag                                             22

<210> SEQ ID NO 50
<211> LENGTH: 25
<212> TYPE: DNA
<213> ORGANISM: Artificial sequence
<220> FEATURE:
<223> OTHER INFORMATION: Synthetic

<400> SEQUENCE: 50
actgtatcat tgctatttc attag                                           25

<210> SEQ ID NO 51
<211> LENGTH: 30
<212> TYPE: DNA
<213> ORGANISM: Artificial sequence
<220> FEATURE:
<223> OTHER INFORMATION: Synthetic

<400> SEQUENCE: 51
tataaaaact ataagaatat ctctacaagg                                30

<210> SEQ ID NO 52
<211> LENGTH: 26
<212> TYPE: DNA
<213> ORGANISM: Artificial sequence
<220> FEATURE:
<223> OTHER INFORMATION: Synthetic

<400> SEQUENCE: 52
aacatataag gtataaaatg gttgag                                    26

<210> SEQ ID NO 53
<211> LENGTH: 25
<212> TYPE: DNA
<213> ORGANISM: Artificial sequence
<220> FEATURE:
<223> OTHER INFORMATION: Synthetic

<400> SEQUENCE: 53
cctcaaccat tttatacctt atatg                                     25

<210> SEQ ID NO 54
<211> LENGTH: 25
<212> TYPE: DNA
<213> ORGANISM: Artificial sequence
<220> FEATURE:
<223> OTHER INFORMATION: Synthetic

<400> SEQUENCE: 54
taactatatt ttctcgtttt ccttg                                     25

<210> SEQ ID NO 55
<211> LENGTH: 30
<212> TYPE: DNA
<213> ORGANISM: Artificial sequence
<220> FEATURE:
<223> OTHER INFORMATION: Synthetic

<400> SEQUENCE: 55
atagaacacc tttacaagaa ataatacctc                                30

<210> SEQ ID NO 56
<211> LENGTH: 19
<212> TYPE: DNA
<213> ORGANISM: Artificial sequence
<220> FEATURE:
<223> OTHER INFORMATION: Synthetic

<400> SEQUENCE: 56
caatccagca tctaccaac                                            19

<210> SEQ ID NO 57
<211> LENGTH: 27
<212> TYPE: DNA
<213> ORGANISM: Artificial sequence
<220> FEATURE:

<223> OTHER INFORMATION: Synthetic

<400> SEQUENCE: 57
aagatcaaca tttcaataga aggtatc 27

<210> SEQ ID NO 58
<211> LENGTH: 25
<212> TYPE: DNA
<213> ORGANISM: Artificial sequence
<220> FEATURE:
<223> OTHER INFORMATION: Synthetic

<400> SEQUENCE: 58
cagcaagcac ttatagttcc attag 25

<210> SEQ ID NO 59
<211> LENGTH: 26
<212> TYPE: DNA
<213> ORGANISM: Artificial sequence
<220> FEATURE:
<223> OTHER INFORMATION: Synthetic

<400> SEQUENCE: 59
tcaaatagat gatatagatg attacg 26

<210> SEQ ID NO 60
<211> LENGTH: 30
<212> TYPE: DNA
<213> ORGANISM: Artificial sequence
<220> FEATURE:
<223> OTHER INFORMATION: Synthetic

<400> SEQUENCE: 60
aatagtagaa ctaaaataaa aaaacctatg 30

<210> SEQ ID NO 61
<211> LENGTH: 25
<212> TYPE: DNA
<213> ORGANISM: Artificial sequence
<220> FEATURE:
<223> OTHER INFORMATION: Synthetic

<400> SEQUENCE: 61
gaaactaggc ataaattaga agaag 25

<210> SEQ ID NO 62
<211> LENGTH: 29
<212> TYPE: DNA
<213> ORGANISM: Artificial sequence
<220> FEATURE:
<223> OTHER INFORMATION: Synthetic

<400> SEQUENCE: 62
tcagcataat catctatatt atctacttg 29

<210> SEQ ID NO 63
<211> LENGTH: 30
<212> TYPE: DNA
<213> ORGANISM: Artificial sequence
<220> FEATURE:
<223> OTHER INFORMATION: Synthetic

<400> SEQUENCE: 63
tcaatatggt taaatatgct aaagatagtg 30

```
<210> SEQ ID NO 64
<211> LENGTH: 23
<212> TYPE: DNA
<213> ORGANISM: Artificial sequence
<220> FEATURE:
<223> OTHER INFORMATION: Synthetic

<400> SEQUENCE: 64
atacccgcat ttactaatcc ttc                                          23

<210> SEQ ID NO 65
<211> LENGTH: 22
<212> TYPE: DNA
<213> ORGANISM: Artificial sequence
<220> FEATURE:
<223> OTHER INFORMATION: Synthetic

<400> SEQUENCE: 65
gattagtaaa tgcgggtatg ac                                           22

<210> SEQ ID NO 66
<211> LENGTH: 22
<212> TYPE: DNA
<213> ORGANISM: Artificial sequence
<220> FEATURE:
<223> OTHER INFORMATION: Synthetic

<400> SEQUENCE: 66
aaagcacatg gacttacagt ac                                           22

<210> SEQ ID NO 67
<211> LENGTH: 21
<212> TYPE: DNA
<213> ORGANISM: Artificial sequence
<220> FEATURE:
<223> OTHER INFORMATION: Synthetic

<400> SEQUENCE: 67
tagaaacggt aatcccatta g                                            21

<210> SEQ ID NO 68
<211> LENGTH: 23
<212> TYPE: DNA
<213> ORGANISM: Artificial sequence
<220> FEATURE:
<223> OTHER INFORMATION: Synthetic

<400> SEQUENCE: 68
taaaagcgaa gcattagtag tag                                          23

<210> SEQ ID NO 69
<211> LENGTH: 30
<212> TYPE: DNA
<213> ORGANISM: Artificial sequence
<220> FEATURE:
<223> OTHER INFORMATION: Synthetic

<400> SEQUENCE: 69
tgataaagta aatagggtag atactactac                                   30

<210> SEQ ID NO 70
<211> LENGTH: 24
<212> TYPE: DNA
<213> ORGANISM: Artificial sequence
<220> FEATURE:
<223> OTHER INFORMATION: Synthetic
```

```
<400> SEQUENCE: 70
aaatacataa ggacaaacca ttac                                          24

<210> SEQ ID NO 71
<211> LENGTH: 23
<212> TYPE: DNA
<213> ORGANISM: Artificial sequence
<220> FEATURE:
<223> OTHER INFORMATION: Synthetic

<400> SEQUENCE: 71
ttttgctgaa atggtagagt atg                                           23

<210> SEQ ID NO 72
<211> LENGTH: 30
<212> TYPE: DNA
<213> ORGANISM: Artificial sequence
<220> FEATURE:
<223> OTHER INFORMATION: Synthetic

<400> SEQUENCE: 72
tatagttttt actgattctt tattgacatc                                    30

<210> SEQ ID NO 73
<211> LENGTH: 19
<212> TYPE: DNA
<213> ORGANISM: Artificial sequence
<220> FEATURE:
<223> OTHER INFORMATION: Synthetic

<400> SEQUENCE: 73
ttggtggagg agttggtac                                                19

<210> SEQ ID NO 74
<211> LENGTH: 22
<212> TYPE: DNA
<213> ORGANISM: Artificial sequence
<220> FEATURE:
<223> OTHER INFORMATION: Synthetic

<400> SEQUENCE: 74
tgataaagaa gaggatgatt cc                                            22

<210> SEQ ID NO 75
<211> LENGTH: 22
<212> TYPE: DNA
<213> ORGANISM: Artificial sequence
<220> FEATURE:
<223> OTHER INFORMATION: Synthetic

<400> SEQUENCE: 75
tcaggtataa atccgcctaa tg                                            22

<210> SEQ ID NO 76
<211> LENGTH: 24
<212> TYPE: DNA
<213> ORGANISM: Artificial sequence
<220> FEATURE:
<223> OTHER INFORMATION: Synthetic

<400> SEQUENCE: 76
caggtactaa accagcagtc atag                                          24

<210> SEQ ID NO 77
<211> LENGTH: 25
```

```
<212> TYPE: DNA
<213> ORGANISM: Artificial sequence
<220> FEATURE:
<223> OTHER INFORMATION: Synthetic

<400> SEQUENCE: 77
ggttttatat gtaagaatga agatg                                       25

<210> SEQ ID NO 78
<211> LENGTH: 23
<212> TYPE: DNA
<213> ORGANISM: Artificial sequence
<220> FEATURE:
<223> OTHER INFORMATION: Synthetic

<400> SEQUENCE: 78
cttagaattt gaagtccagt ttg                                         23

<210> SEQ ID NO 79
<211> LENGTH: 20
<212> TYPE: DNA
<213> ORGANISM: Artificial sequence
<220> FEATURE:
<223> OTHER INFORMATION: Synthetic

<400> SEQUENCE: 79
gaagtttttg gcataggaac                                             20

<210> SEQ ID NO 80
<211> LENGTH: 23
<212> TYPE: DNA
<213> ORGANISM: Artificial sequence
<220> FEATURE:
<223> OTHER INFORMATION: Synthetic

<400> SEQUENCE: 80
tcattttctt ttaatggtgt atc                                         23

<210> SEQ ID NO 81
<211> LENGTH: 23
<212> TYPE: DNA
<213> ORGANISM: Artificial sequence
<220> FEATURE:
<223> OTHER INFORMATION: Synthetic

<400> SEQUENCE: 81
aaaaggctat ttagaatctg aag                                         23

<210> SEQ ID NO 82
<211> LENGTH: 30
<212> TYPE: DNA
<213> ORGANISM: Artificial sequence
<220> FEATURE:
<223> OTHER INFORMATION: Synthetic

<400> SEQUENCE: 82
cattatctcc ataagtatag aaaactctac                                  30

<210> SEQ ID NO 83
<211> LENGTH: 24
<212> TYPE: DNA
<213> ORGANISM: Artificial sequence
<220> FEATURE:
<223> OTHER INFORMATION: Synthetic

<400> SEQUENCE: 83
```

```
tggtgatata gcaaaaagta tagc                                              24

<210> SEQ ID NO 84
<211> LENGTH: 26
<212> TYPE: DNA
<213> ORGANISM: Artificial sequence
<220> FEATURE:
<223> OTHER INFORMATION: Synthetic

<400> SEQUENCE: 84
ccctacaata attttaggtt cttcag                                            26

<210> SEQ ID NO 85
<211> LENGTH: 21
<212> TYPE: DNA
<213> ORGANISM: Artificial sequence
<220> FEATURE:
<223> OTHER INFORMATION: Synthetic

<400> SEQUENCE: 85
gtgggaaaaa taaatctgaa g                                                 21

<210> SEQ ID NO 86
<211> LENGTH: 24
<212> TYPE: DNA
<213> ORGANISM: Artificial sequence
<220> FEATURE:
<223> OTHER INFORMATION: Synthetic

<400> SEQUENCE: 86
gcttaattct acagtaaaat gctg                                              24

<210> SEQ ID NO 87
<211> LENGTH: 30
<212> TYPE: DNA
<213> ORGANISM: Artificial sequence
<220> FEATURE:
<223> OTHER INFORMATION: Synthetic

<400> SEQUENCE: 87
gtaatgatga acttaaaaaa tcaggtattg                                        30

<210> SEQ ID NO 88
<211> LENGTH: 22
<212> TYPE: DNA
<213> ORGANISM: Artificial sequence
<220> FEATURE:
<223> OTHER INFORMATION: Synthetic

<400> SEQUENCE: 88
attccatgag ccacataagg ag                                                22

<210> SEQ ID NO 89
<211> LENGTH: 26
<212> TYPE: DNA
<213> ORGANISM: Artificial sequence
<220> FEATURE:
<223> OTHER INFORMATION: Synthetic

<400> SEQUENCE: 89
aaacagtcaa atatgagtta tagtgc                                            26

<210> SEQ ID NO 90
<211> LENGTH: 26
<212> TYPE: DNA
<213> ORGANISM: Artificial sequence
```

```
<220> FEATURE:
<223> OTHER INFORMATION: Synthetic

<400> SEQUENCE: 90
aaatctggta tacttttatc cttttc                                              26
```